United States Patent
Rapacki et al.

(10) Patent No.: US 6,635,214 B2
(45) Date of Patent: *Oct. 21, 2003

(54) MANUFACTURING CONDUITS FOR USE IN PLACING A TARGET VESSEL IN FLUID COMMUNICATION WITH A SOURCE OF BLOOD

(75) Inventors: Alan R. Rapacki, Redwood City, CA (US); Dean F. Carson, Mountain View, CA (US); A. Adam Sharkawy, Union City, CA (US)

(73) Assignee: Ventrica, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/394,119

(22) Filed: Sep. 10, 1999

(65) Prior Publication Data

US 2003/0015816 A1 Jan. 23, 2003

(51) Int. Cl.⁷ .................. B29C 39/02; B29C 41/02; B29C 45/14; B29C 65/70
(52) U.S. Cl. ............ 264/250; 264/299; 623/1.49; 128/897; 128/898
(58) Field of Search ................ 264/249, 263, 264/271.1, 275, 277, 299, 319, 320, 328.1, 250; 623/1.49, 1.14; 606/194; 128/898, 897

(56) References Cited

U.S. PATENT DOCUMENTS

| | | | |
|---|---|---|---|
| 2,127,903 A | | 8/1938 | Bowen |
| 3,042,021 A | | 7/1962 | Read |
| 3,901,965 A | * | 8/1975 | Honeyman, III ......... 264/328.1 |
| 3,907,401 A | * | 7/1976 | Lubeck ................ 264/261 |
| 4,284,459 A | * | 8/1981 | Patel et al. ............ 264/275 |
| 4,822,341 A | * | 4/1989 | Colone ................ 604/175 |
| 4,873,043 A | * | 10/1989 | Meyers ............... 264/328.1 |
| 4,955,856 A | | 9/1990 | Phillips |
| 4,955,899 A | | 9/1990 | Della Corna |
| 4,995,857 A | * | 2/1991 | Arnold ................ 600/16 |
| 5,054,484 A | | 10/1991 | Hebeler |
| 5,302,336 A | * | 4/1994 | Hartel et al. ........... 264/263 |

(List continued on next page.)

FOREIGN PATENT DOCUMENTS

| | | |
|---|---|---|
| WO | WO 88/06865 | 9/1988 |
| WO | WO 98/16174 | 4/1998 |
| WO | WO 98/19630 | 5/1998 |
| WO | WO 98/38939 | 9/1998 |
| WO | WO 99/65409 | 12/1999 |

OTHER PUBLICATIONS

Jomed Direction, product literature, no date.

Primary Examiner—Angela Ortiz
(74) Attorney, Agent, or Firm—Hoekendijk & Lynch, LLP

(57) ABSTRACT

Methods and devices for manufacturing a conduit for placing a target vessel in fluid communication with a source of blood, such as a heart chamber containing blood. The conduit includes first and second portion adapted to be placed in fluid communication with a heart chamber and a target vessel. The conduit lies on the exterior of the myocardium between the blood source and the target vessel and delivers blood in multiple directions within the lumen of the target vessel. The conduit, which may be formed of any suitable synthetic vascular graft material, is generally T-shaped with the leg having two free ends disposed in the target vessel, preferably being secured thereto via a suture-free attachment. The conduit comprises vascular graft material and may be manufactured various ways, such as molding a conduit from any suitable biocompatible material or fabricating a conduit from one or more pieces of vascular graft material.

23 Claims, 23 Drawing Sheets

U.S. PATENT DOCUMENTS

| | | | |
|---|---|---|---|
| 5,330,500 A | | 7/1994 | Song |
| 5,356,587 A | * | 10/1994 | Mitsui et al. ............... 264/263 |
| 5,443,497 A | | 8/1995 | Venbrux |
| 5,478,309 A | | 12/1995 | Sweezer et al. |
| 5,643,340 A | | 7/1997 | Nunokawa |
| 5,653,743 A | | 8/1997 | Martin |
| 5,683,640 A | * | 11/1997 | Miller et al. ............... 264/255 |
| 5,655,548 A | | 12/1997 | Nelson et al. |
| 5,713,950 A | * | 2/1998 | Cox ........................... 623/66 |
| 5,755,682 A | * | 5/1998 | Knudson et al. .............. 604/8 |
| 5,755,778 A | | 5/1998 | Kleshinski |
| 5,836,316 A | | 11/1998 | Plaia et al. |
| 5,968,089 A | | 10/1999 | Krajicek |
| 5,972,017 A | | 10/1999 | Berg et al. |
| 5,984,956 A | * | 11/1999 | Tweden et al. ................ 623/1 |
| 5,989,276 A | | 11/1999 | Houser et al. |
| 6,019,788 A | | 2/2000 | Butters et al. |
| 6,035,856 A | | 3/2000 | LaFontaine et al. |
| 6,053,942 A | * | 4/2000 | Eno et al. ................... 623/1.15 |
| 6,102,941 A | * | 8/2000 | Tweden et al. ................ 623/1 |
| 6,165,185 A | | 12/2000 | Shennib et al. |
| 6,176,864 B1 | | 1/2001 | Chapman |
| 6,197,050 B1 | * | 3/2001 | Eno et al. ................... 623/1.36 |
| 6,214,041 B1 | * | 4/2001 | Tweden et al. ............ 623/1.17 |
| 6,241,741 B1 | | 6/2001 | Duhaylongsond et al. |
| 6,250,305 B1 | * | 6/2001 | Tweden ..................... 128/898 |
| 6,251,133 B1 | * | 6/2001 | Richter et al. ............. 623/1.16 |

* cited by examiner

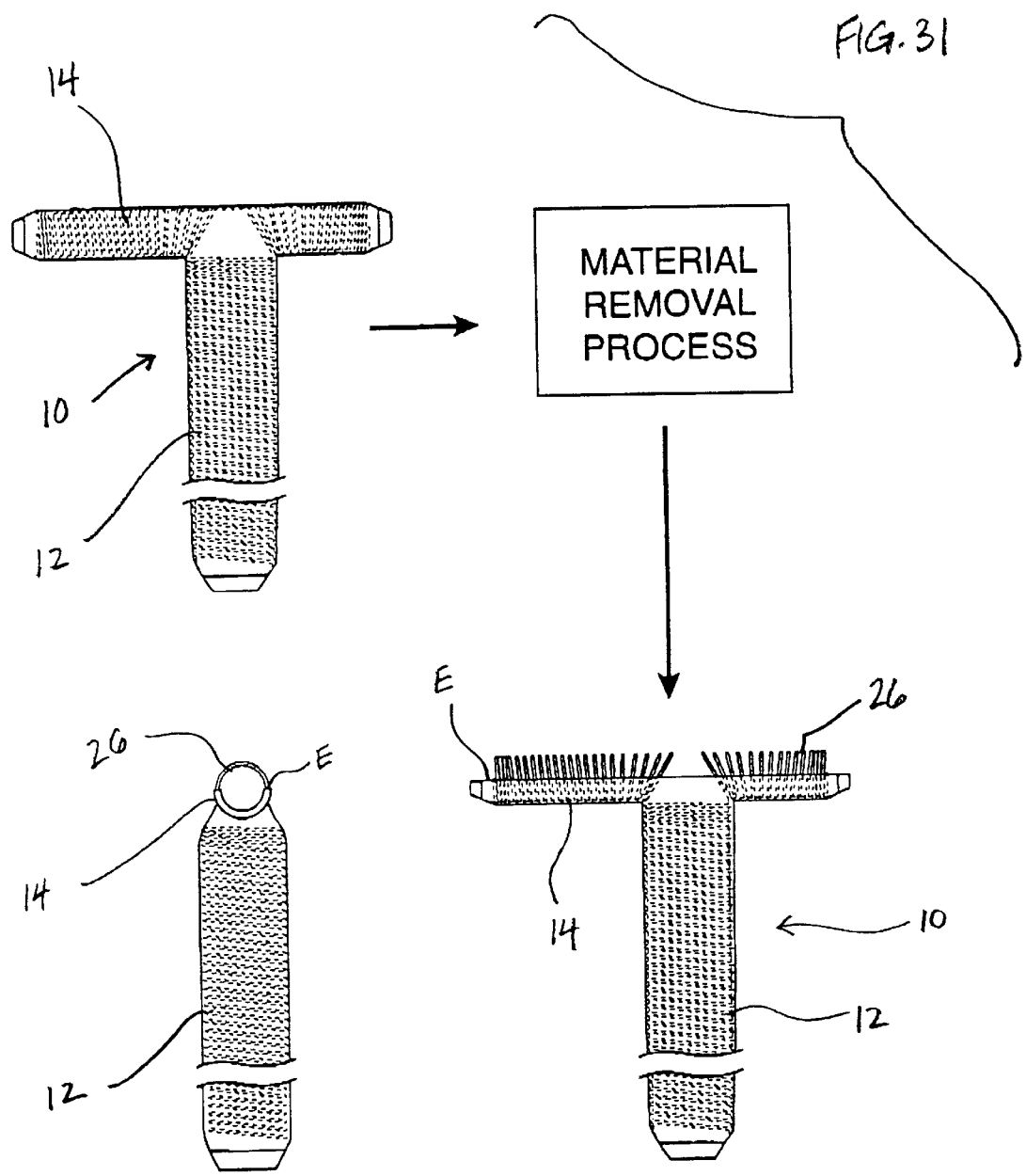

MANUFACTURING CONDUITS FOR USE IN PLACING A TARGET VESSEL IN FLUID COMMUNICATION WITH A SOURCE OF BLOOD

BACKGROUND OF THE INVENTION

1. Field of the Invention

The invention relates to methods and devices for manufacturing a conduit for placing a target vessel in fluid communication with a source of blood, and more particularly placing a coronary vessel in fluid communication with a heart chamber containing blood.

2. Description of Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new and improved treatments.

Coronary artery disease is currently treated by interventional procedures such as percutaneous transluminal coronary angioplasty (PTCA), coronary stenting and atherectomy, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockage(s). When successful, these procedures restore blood flow to myocardial tissue that had not been sufficiently perfused due to the occlusion.

An alternative, recently proposed treatment places the target vessel in fluid communication with a heart chamber containing blood, for example, the left ventricle. Blood flows from the ventricle into a conduit that is in fluid communication with the target vessel. Some of the challenges associated with these procedures include delivering and deploying the conduit in the patient's body, and in particular properly positioning the conduit with respect to the heart chamber and the target vessel.

The continued improvement and refinement of existing treatments and the search for new treatments are indicative of the significant effort that continues to be expended in order to develop better and more efficient ways of revascularizing the heart.

Accordingly, there is a need in the art for improved methods and devices that are capable of being used quickly, easily and in a repeatable manner to carry out cardiac revascularization successfully and economically. Consequently, there is a need in the art for methods and devices for manufacturing conduits that will meet one or more of these needs.

SUMMARY OF THE INVENTION

According to one embodiment of the invention, methods and devices are provided for manufacturing a conduit for use in placing a target vessel in fluid communication with a source of blood. One method includes steps of providing a biocompatible material suitable for use in delivering blood, and forming the biocompatible material into a conduit comprising first and second portions disposed transverse to each other and having lumens in fluid communication. The first conduit portion is formed with at least one inlet configured to be positioned in fluid communication with a heart chamber containing blood, and at least a part of the first conduit portion has sufficient rigidity to prevent collapse during myocardial contraction when disposed in or secured to myocardial tissue. The second conduit portion is formed with at least one outlet configured to be placed at least partially within the lumen of a target vessel in fluid communication with the vessel, and at least a part of the second conduit portion has sufficient resiliency to allow the second conduit portion to substantially conform to the contour of the target vessel.

Another method includes steps of providing a mold having a cavity configured to form a conduit including first and second portions disposed transverse to each other, wherein a conduit corresponding to the cavity is suitable for use in placing a source of blood in fluid communication with the lumen of a target vessel, placing a biocompatible moldable material in the mold cavity, subjecting the material to conditions that mold the material into a conduit having a desired configuration, and separating the mold and the conduit.

Another method includes step of providing a mold having a cavity including first and second portions disposed transverse to each other, positioning a mandrel in the mold cavity, the mandrel having first and second portions substantially corresponding to the first and second portions of the mold cavity, and forcing a moldable material into the mold cavity and around the first and second portions of the mandrel into the first and second portions of the mold cavity. The method further includes subjecting the material to conditions sufficient to set the material in a desired configuration, removing the mandrel from the mold, and separating the mandrel and the material to produce a conduit comprising first and second portions that are disposed transverse to each other and have lumens in fluid communication with each other.

Another method includes steps providing a mandrel including first and second portions disposed transverse to each other, the first and second portions of the mandrel defining at least one external surface corresponding to an interior surface of a desired conduit configuration, disposing a biocompatible moldable material on the external surface of the mandrel, subjecting the material to conditions that mold the material into a conduit having the desired configuration, and separating the conduit from the mandrel.

Still another method includes steps of forming biocompatible material into a conduit comprising first and second portions disposed transverse to each other and having lumens in fluid communication, forming the first conduit portion with at least one inlet configured to be placed in fluid communication with a heart chamber containing blood, and providing at least a part of the first conduit portion with sufficient rigidity to prevent collapse during myocardial contraction when disposed in or secured to myocardial tissue. The second conduit portion is formed with at least one outlet configured to be placed at least partially within the lumen of a target vessel in fluid communication with the vessel, and this step is carried out so as to form the first conduit portion with a full tubular configuration that extends substantially 360° in cross-section, and the second conduit portion with a partial tubular configuration that extends less than 360° in cross-section.

A mold constructed according to the invention includes a base defining a mold cavity, wherein the mold cavity has first and second portions configured to form a conduit including first and second portions, and wherein the first and second portions of the mold cavity are disposed transverse to each other to form a conduit with first and second conduit portions in fluid communication with each other and adapted to place the lumen of a target vessel in fluid communication with a heart chamber containing blood.

Another method according to the invention includes steps of providing first and second hollow members each of which has a lumen, forming an opening that extends into the lumen of the first hollow member, positioning one of the first and second ends of the second hollow member adjacent the opening in the first hollow member, and joining the one end of the second hollow member to the first hollow member with the lumens of the first and second hollow members sealed together in fluid communication.

BRIEF DESCRIPTION OF THE DRAWINGS

The invention will be better understood from the following detailed description of preferred embodiments thereof, taken in conjunction with the accompanying drawing figures, wherein:

FIG. 1A is a transverse sectional view taken along line A—A in FIG. 1;

FIG. 1B is a plan view of the conduit shown in FIG. 1;

FIG. 31 schematically illustrates the formation of a conduit according to another embodiment of the invention;

FIG. 32 is an end elevation view of the conduit shown in FIG. 31;

DETAILED DESCRIPTION OF PREFERRED EMBODIMENTS

The present invention provides methods and devices for manufacturing a conduit that is placed in a patient's body to establish a flow path between a source of blood and a target vessel of the patient's vascular system. In a preferred application, the source of blood is a heart chamber containing oxygenated blood and the target vessel is a coronary artery or vein. It will be recognized, however, that the conduit may be used to form a blood flow path between other hollow body structures. Also, as used herein, source of blood refers to any blood-containing structure, while oxygenated blood refers to blood containing some level of oxygen. The conduit may be used to bypass a partial or complete occlusion in the target vessel; alternatively or additionally, the conduit may be used to supplement blood flow (native or other) that is already present in the target vessel.

The Figures show several conduit configurations in order to describe various aspects of exemplary embodiments of the present invention. It will be recognized, though, that these conduits represent only a few of the numerous constructions that may be manufactured according to the principles of the invention. For example, the conduit may be manufactured so as to have any of the constructions described in co-pending, commonly owned application Ser. No. 09/393,131, filed Sept. 10, 1999, and entitled "Conduits For Use in Placing a Target Vessel in Fluid Communication With a Source of Blood," the entire subject matter of which is incorporated herein by reference.

In its most preferred form, the conduit of the invention include a first conduit portion having at least one inlet adapted to be placed in communication with a source of blood and a second portion having at least one outlet adapted to be placed in communication with the lumen of a target vessel. The first and second conduit portions may be defined by a single unitary member or several members that are attached or formed into a desired configuration. The first and second conduit portions are transverse to each other and have lumens that meet at a junction. For example, the first and second conduit portions have respective axes that extend transversely to each other to form a predetermined angle, the angle preferably being within a desired range that achieves acceptable flow characteristics.

Figure 1:
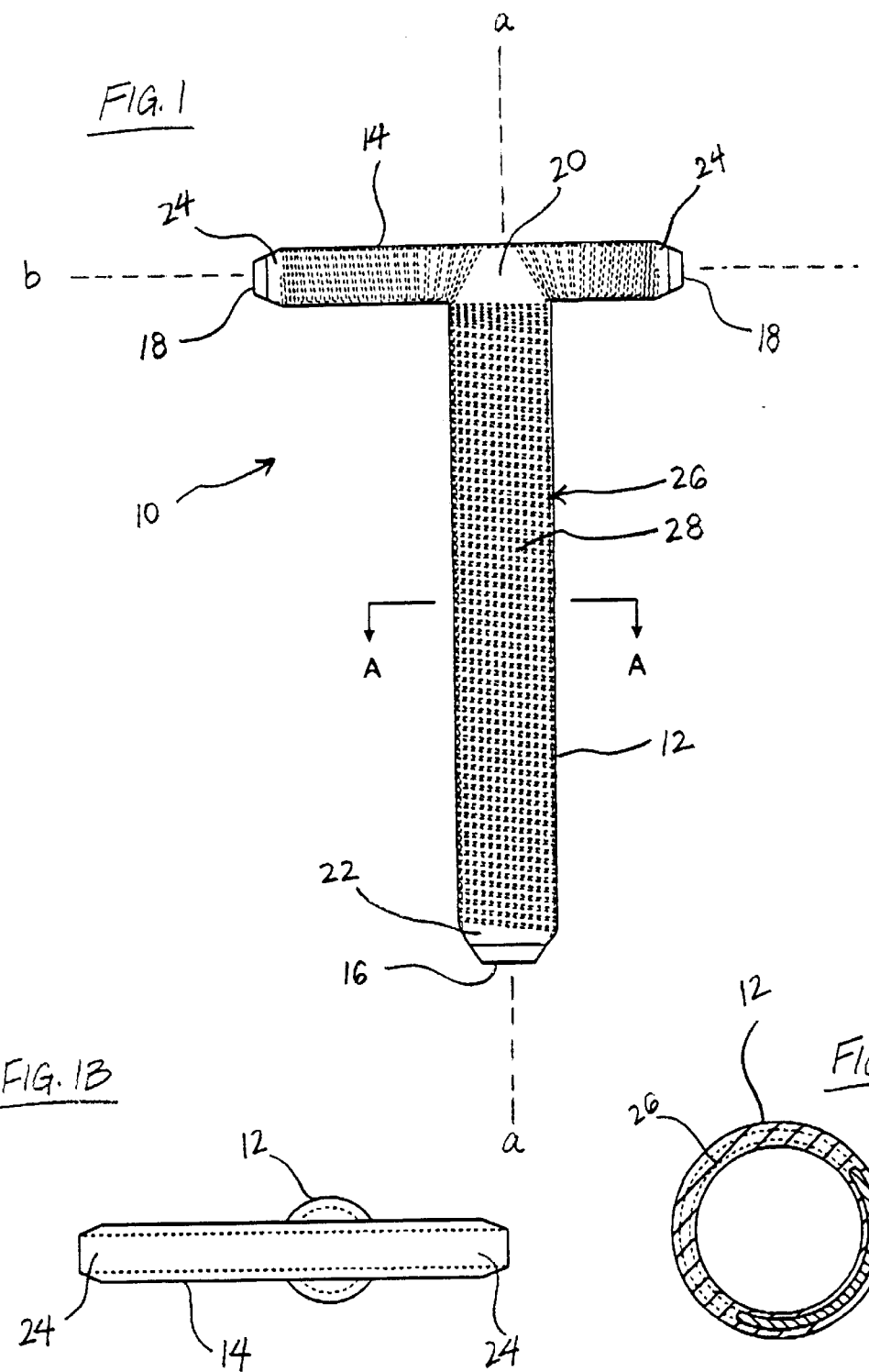
FIG. 1 is a front elevation view of a conduit constructed according to one embodiment of the invention for placing a source of blood in fluid communication with a target vessel.
Figure 2:
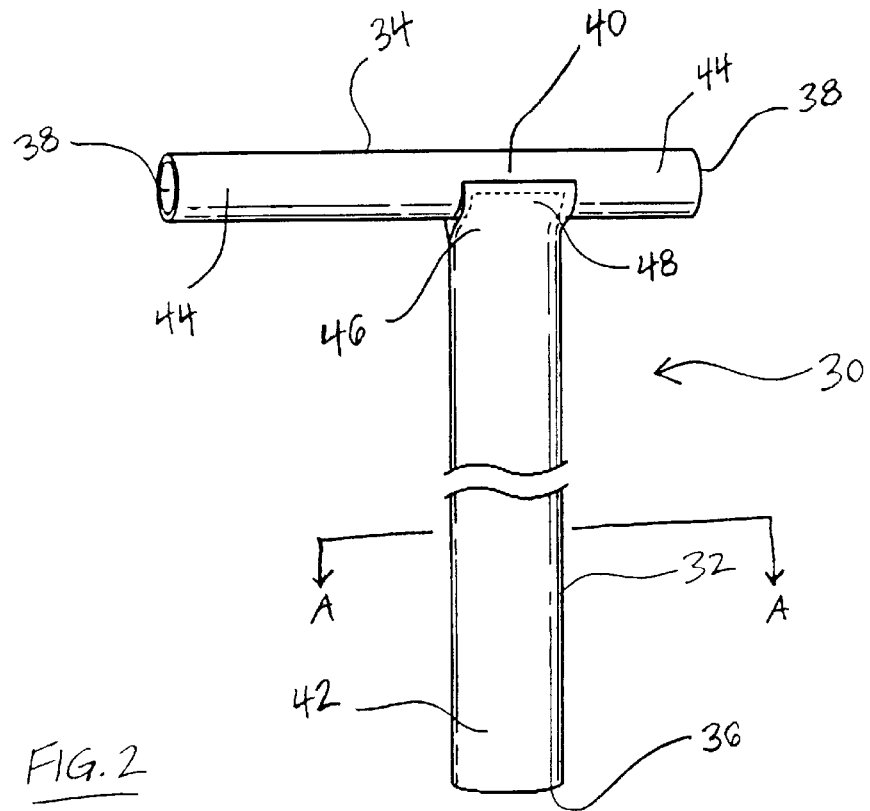
FIG. 2 is a perspective view of a conduit constructed according to another embodiment of the invention for placing a target vessel in fluid communication with a source of blood.

FIGS. 1 and 2 will be discussed in some detail for sake of explanation and clarity. Referring to FIGS. 1, 1A and 1B, a conduit 10 includes a first conduit portion 12 and a second conduit portion 14. The first conduit portion 12 has an inlet 16 that is placed in fluid communication with a source of blood, and the second conduit portion 14 has a pair of outlets 18 that are placed in fluid communication with a target vessel. It will be appreciated that the first conduit portion 12 may have more than one inlet and the second conduit portion 14 may have one, two or more outlets. The first and second conduit portions 12, 14 have lumens in fluid communication with each other.

The conduit 10 is generally T-shaped with the first and second conduit portions 12, 14 meeting at a junction 20 such that their respective axes a, b are substantially perpendicular. It should be noted, though, that according to the invention the axes a, b of the first and second conduit portions 12, 14 could be disposed non-perpendicularly. For example, rather than forming a 90° (or substantially 90°) angle, the axes a, b could extend transversely to each other to form an acute or obtuse angle (depending on which side the angle is measured with respect to axis a in FIG. 1).

The first conduit portion 12 has a free end 22 defining the inlet 16 while the second conduit portion 14 has a pair of free ends 24 defining the outlets 18. The free ends 22, 24 may be integral extensions of their respective conduit portions or they may comprise separate members secured to the conduit. One or more of the free ends 22, 24 may be beveled (or otherwise configured) for easier introduction into the target vessel. The ends 22, 24 of the conduit portions 12, 14 are preferably formed of a flexible, relatively atraumatic material that will not damage the endothelial cells lining the intimal surface of the target vessel, particularly during placement of the device.

The conduit inlet 16 or outlets 18 may be located at positions other than those shown in the Figures, e.g., at one or more points along the length of the conduit. Similarly, in the illustrated embodiment the first conduit portion 12 (axis a) is offset in that it does not bisect the second conduit portion 14 (axis b); this provides the second conduit portion with different size legs extending away from the first conduit portion. Configuring the target vessel portion of the conduit 10 with shorter and longer legs may be useful in introducing the conduit into the target vessel. It should nonetheless be recognized that the first conduit portion 12 may be centrally located along the axis b of the second conduit portion 14 to provide legs of equal length, or it may be offset from the axis b a greater distance than shown in FIG. 1.

According to one preferred embodiment, the methods and devices of the invention are used to form a conduit that is provided with a reinforcing component having sufficient strength to ensure that the conduit remains open during use by preventing or reducing the likelihood of the conduit kinking or collapsing. The reinforcing component may be integrally formed with the conduit or it may comprise a separate member secured thereto. One embodiment of a reinforcing component 26 is shown in FIG. 1 (in phantom) and comprises a plurality of coils 28 which extend over the first and second conduit portions 12, 14. As seen from FIG. 1A, the reinforcing component 26 is preferably encased in the body of the conduit 10 which prevents contact between tissue and the reinforcing coils 28.

In the illustrated embodiment, the spacing, as well as the size and material of construction, of the coils 28 may be used to determine the amount of structural support provided by the reinforcing component 26. As such, these variables may be selected to produce a conduit having desired characteristics. For example, one of the first and second conduit portions 12, 14 may be made more rigid or flexible than the other by varying the pitch of the coils, the thickness of the wire forming the coils, the material forming the coils, etc., on the portions. Further, the reinforcing component 26 may comprise a single coil, a first coil for the first conduit portion and a second coil for the second conduit portion, a first coil for the first conduit portion and two separate coils for the two free legs of the second conduit portion, etc. Finally, it will be noted that the reinforcing component may have a non-coiled configuration, e.g., a stent or stent-like construction, and may comprise a single member or a plurality of discrete members.

The second conduit portion 14 is relatively flexible to allow it to yield slightly and follow the contour of the target vessel (not shown) while being placed therein. The first conduit portion 12 may be more rigid than the second conduit portion 14, particularly if the blood source is a heart chamber and the first conduit portion 12 is placed in (or secured to) myocardial tissue. In this case, the first conduit portion 12 would preferably be relatively rigid to remain open during myocardial contraction. The junction 20 of the first and second conduit portions 12, 14 is essentially unreinforced in the embodiment shown in FIGS. 1 and 1A, but it could be stiffened, e.g., by disposing one or more coils 28 of the reinforcing component 26 at or adjacent the junction 20.

Whereas the conduit 10 (without the reinforcing component 26) is formed of one piece of material, the conduit 30 shown in FIG. 2 is formed of discrete pieces of material. The conduit 30 includes a first conduit portion 32 and a second conduit portion 34 which correspond to the first and second conduit portions of the previous embodiments. The first conduit portion 32 has at least one inlet 36 while the second conduit portion 64 has at least one outlet 38. The conduit portions 32, 34 are joined at a junction 40 by suitable means, e.g., adhesives, thermal bonding, mechanical attachment, etc., which are described further below. The first conduit portion 32 has a free end 42 defining an inlet 36 and the second conduit portion 34 has free ends 44 defining two outlets 38.

As described further below, the first conduit portion 32 of this embodiment has an opposite end 46 which is bifurcated into two flaps 48 each of which is secured to the conduit portion 34 by any suitable means. The edges of the flaps 48 may be tapered or feathered (as shown) to make a smooth transition with the exterior of the second conduit portion 34, thereby minimizing the amount of material to be introduced into the lumen of the target vessel. It also may be preferable to minimize the wall thickness of the material used to form the conduit to further reduce the amount of material that must be accommodated in the target vessel lumen, without sacrificing preferential blood flow characteristics or the structural integrity of the conduit.

Figure 2A:
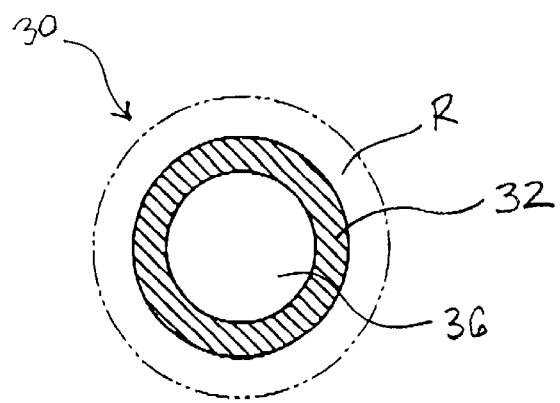
FIG. 2A is a transverse sectional view taken along line A—A in FIG. 2.

The illustrated conduit 30 may include a reinforcing component such as 26 that is coupled to or formed with the body of the conduit. Alternatively, as shown in phantom in FIG. 2A, the conduit 30 could include a reinforcing layer R. The layer R could be a mechanical component secured to the conduit or a chemical substance that is partially or completely applied to the exterior (or interior) of the conduit wall.

Figure 3A:
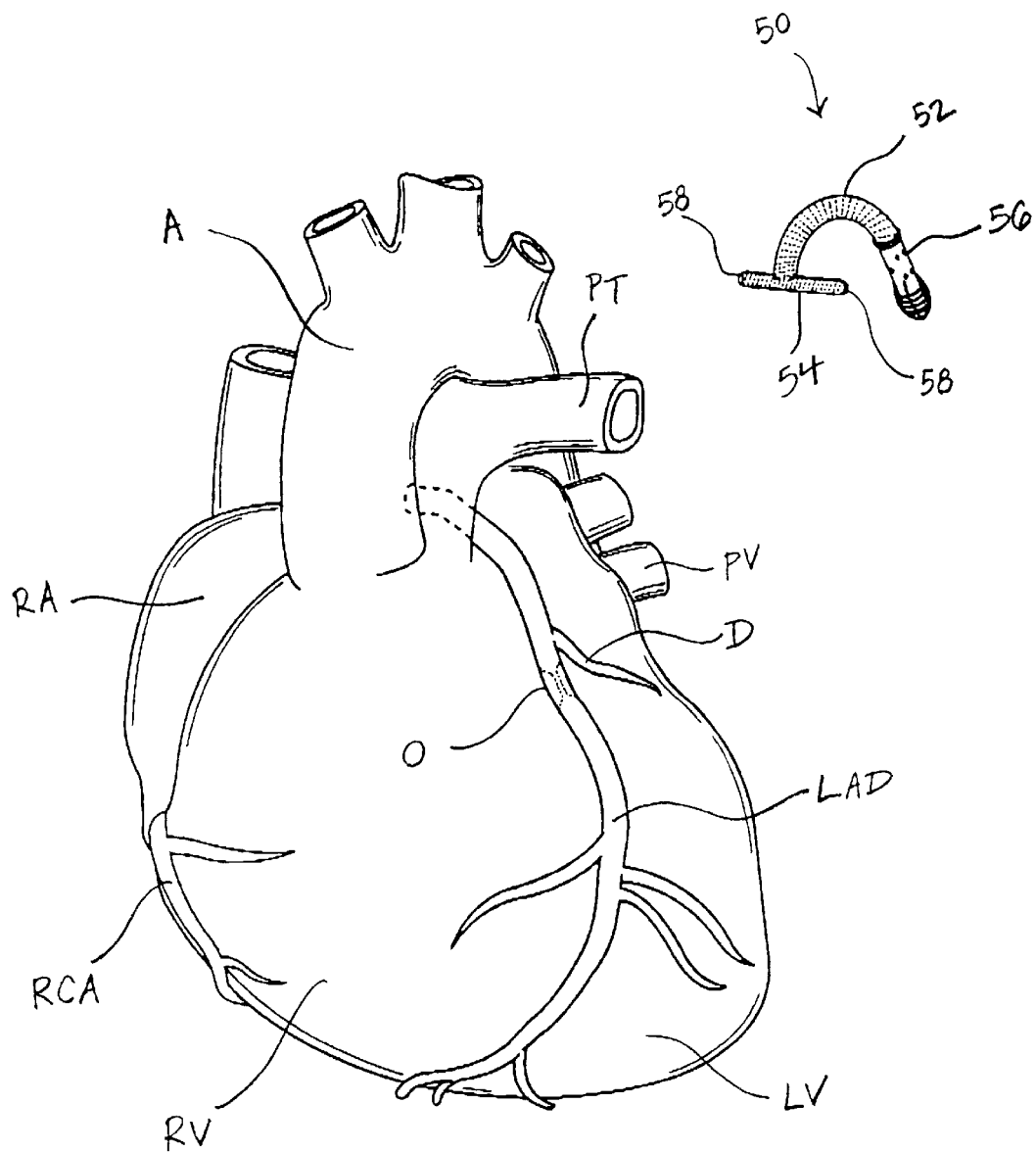
FIG. 3A is a perspective anterior view of a heart with an occluded coronary artery and a conduit constructed according to the invention.

An exemplary manner in which the conduits of the invention may be used to establish a blood flow path between a target vessel and a source of blood will be explained briefly with respect to FIGS. 3A–3C. FIG. 3A is an anterior view of a heart H showing the left ventricle LV, right ventricle RV, right atrium RA, aorta A, pulmonary trunk PT and pulmonary veins PV. The left coronary artery, including its left anterior descending branch LAD, is visible in this view, as is the right coronary artery RCA. Also shown is a diagonal branch D of the LAD. The coronary arteries run along the myocardium and deliver oxygenated blood to the myocardial tissue. An occlusion or stenosis O partially (or completely) obstructs the lumen of the LAD, which results in inadequate or no blood flow to the myocardial tissue fed by the portion of the LAD that is downstream of the occlusion O.

FIG. 3A also shows a conduit 50 which is constructed according to the invention and is positioned adjacent the heart H. The conduit 50 includes first and second conduit portions 52, 54 adapted to be placed in communication with a heart chamber and a target vessel, respectively. The conduit 50 includes a device 56 for establishing communication with a heart chamber while securing the conduit in the desired position, as well as a reinforcing component for supporting the walls of the conduit. The device 56 is described in the aforementioned co-pending application the subject matter of which has been incorporated herein by reference.

Figure 3B:
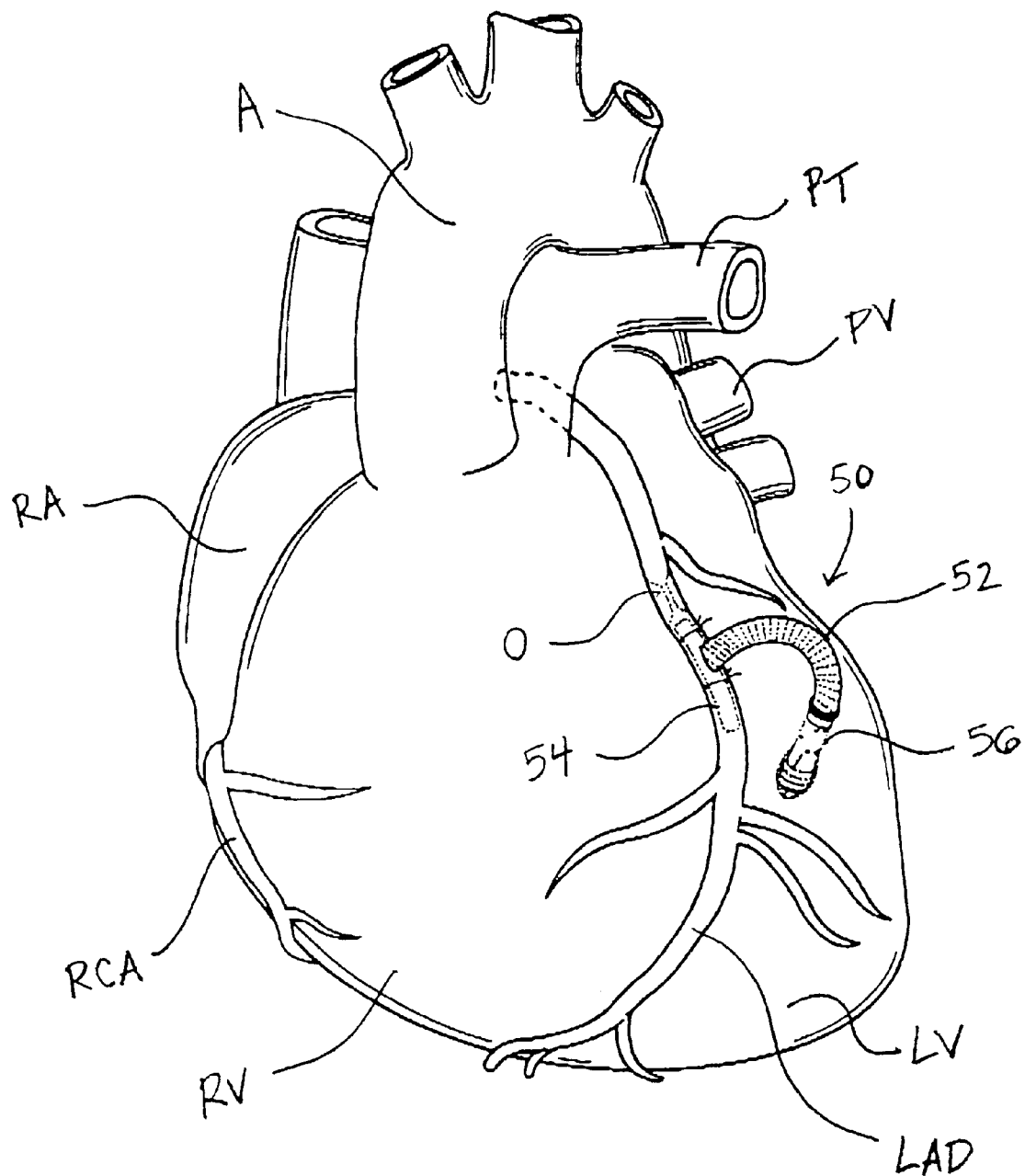
FIG. 3B is a perspective view of the heart shown in FIG. 3A after the conduit has been deployed to bypass the occluded artery.

FIG. 3B depicts the heart H shown in FIG. 3A after the conduit 50 has been deployed. The device 56 is inserted into the tissue of the myocardium so that its distal end is in fluid communication with the left ventricle LV. The first conduit portion 52 extends from the device 56 to the LAD, and the second conduit portion 54 enters the LAD at a location distal to the occlusion O, the portion 54 contacting and sealing against the luminal surface of the vessel wall. As a result, blood flows from the left ventricle LV into the conduit 50 and the LAD to perfuse myocardial tissue distal to the occlusion O.

Figure 3C:
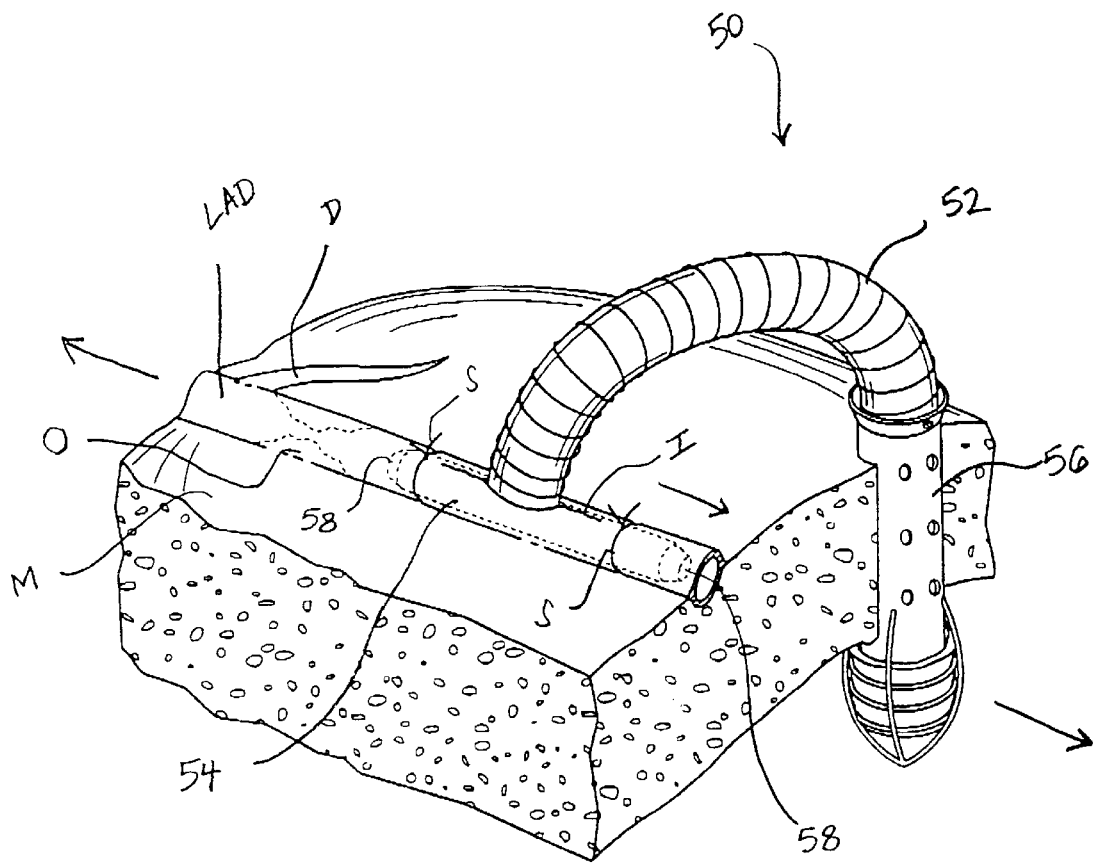
FIG. 3C is an enlarged, fragmentary sectional view of the heart and conduit illustrated in FIG. 3B.

FIG. 3C is an enlarged view of a portion of the heart H shown in FIG. 3B. The device 56 is shown positioned in the myocardium M so as to communicate with the left ventricle LV. The device 56 is preferably sized so as to extend completely through the myocardium M and project into the left ventricle LV, slightly beyond the exterior of the myocardium. Alternatively, the device 56 could terminate within the myocardium with a distal segment of the first conduit portion 52 extending into the left ventricle, or the device 56 omitted and the first conduit portion 52 positioned in the myocardium. In any case, as explained in the aforementioned co-pending application, it may be desirable to first measure the thickness of the myocardium, either approximately or precisely, at the area that will receive the device 56 (or the distal segment of the first conduit portion 52). The device 56 may then be placed with its ends properly positioned with respect to the left ventricle and the exterior of the myocardium.

The second conduit portion 54 includes two outlets 58 placed in the lumen of the LAD through an incision I; in the illustrated embodiment, the conduit portion 54 is secured in place by suture S. The second conduit portion 54 will typically be placed in the target vessel distal to the occlusion by a distance that permits easier introduction into the lumen, as opposed to entering a diseased or stenosed section of the vessel. This results in a space located between the occlusion O and the conduit outlet 58 that is disposed nearest the occlusion (the outlet to the left in FIG. 4C). Thus, if the conduit does not provide blood flow toward the occlusion O, this space, and more particularly the myocardial tissue fed by this section of the LAD, may become ischemic, particularly if the occlusion totally blocks any native flow through the vessel from an upstream source.

Accordingly, as explained in the aforementioned co-pending application, the conduits of the invention are preferably configured to deliver blood into the target vessel in multiple directions to fully revascularize the myocardial tissue perfused by the vessel. As shown in FIG. 3C, blood flows into the second conduit portion 54 and exits the outlets 58 in more than one direction, as indicated by the arrows. The illustrated directions are along a common axis and opposite each other, but it will be recognized that this is only one possible arrangement to achieve multidirectional flow in the target vessel.

Figure 4:
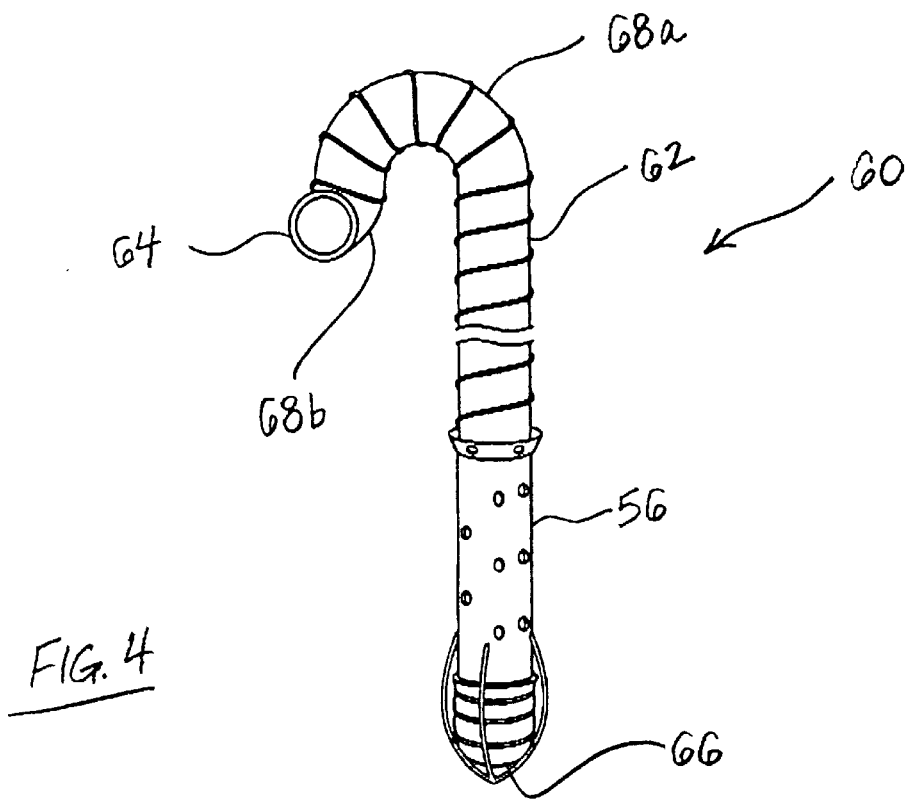
FIG. 4 is a perspective view of a conduit constructed according to another embodiment of the invention for placing a target vessel in fluid communication with a source of blood.

FIG. 4 shows a conduit 60 constructed according to another embodiment of the invention. The conduit 60 includes a first conduit portion 62 and a second conduit portion 64, the device 56 being coupled to the portion 64.

The first conduit portion 62 has an inlet 66 and includes multiple bends 68a, 68b which serve to align the second conduit portion 64 with the axis of the target vessel. The conduit 60 is generally L-shaped and second conduit portion 64 has an outlet that directs blood into the target vessel. The bends 68a, 68b may be imparted to the conduit 60 in various manners. For example, a mandrel having a shape and size complementary to that of the conduit 60 may be dipped in a suitable biocompatible material, e.g., silicone, and then heated or subjected to other conditions to cause the material to set and form the desired conduit configuration. Two or more bends are imparted to the conduit and preferably lie in two different transverse planes, for example, substantially perpendicular planes as shown in FIG. 4. It should be recognized that the particular angle(s) selected, as well as the overall configuration of the conduit, may be varied from that depicted depending on the application and user preference.

Figure 5:
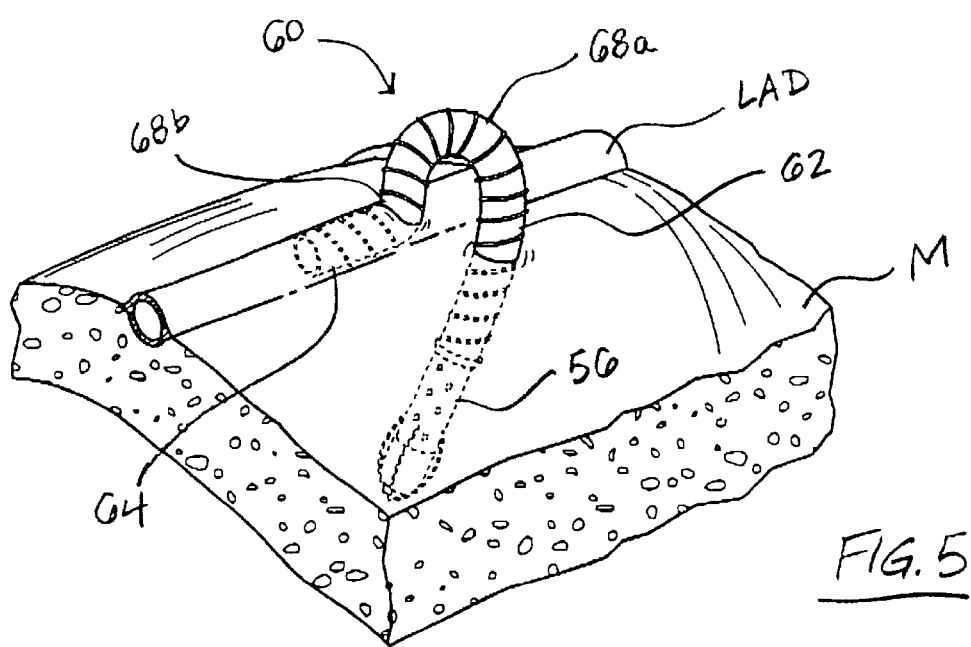
FIG. 5 is an enlarged, fragmentary sectional view of the heart illustrated in FIG. 3A showing the conduit of FIG. 4 positioned in the coronary artery.

FIG. 5 shows the conduit 60 positioned in the target vessel (the LAD in the illustrated embodiment) and the heart chamber (the left ventricle) in the same manner as the conduit 50 shown in FIGS. 3A–3C. As shown, the multiple bends 68a, 68b of the second conduit portion 64 direct its outlets generally along the axis of the target vessel, although alternative configurations could be used as well. One benefit of this embodiment is that when used in an external manner (i.e., a significant portion of the conduit is exterior to the myocardium) the configuration allows the conduit to be placed through the myocardium at a location that is spaced from the coronary vessel. This is contrast to placing a conduit so that it passes transmurally through the myocardium and the inner or posterior wall of the target vessel to deliver blood into the vessel lumen. This embodiment thus provides flexibility insofar as the portion of the conduit communicating with the heart chamber may be placed through the myocardium at different locations while still accessing the target vessel in the desired manner, which may be useful in situations that present limited access to the heart or target vessels.

It will be appreciated that the size of the conduit and thus the methods and for manufacturing the conduits will vary depending on the application. In short, each conduit portion has a length, a diameter (or a different dimension if the cross-section is non-circular) and a wall thickness, and the methods and devices of the invention may be utilized and modified to control one or more of these dimensions, for example, to obtain desired flow characteristics or adapt the conduit to a given application.

The conduit is preferably sized and configured to form a blood flow path that is equal or substantially equal, in volume of blood carried, to the blood flow path defined by the native vessel. In other words, the conduit preferably defines an inner diameter that equals or substantially equals the inner diameter of the native vessel. As a result, when placed in the target vessel the conduit allows a sufficient volume of blood to flow through the target vessel. If the target vessel is a coronary artery, this ensures that blood will flow to the distal vasculature and perfuse the myocardial tissue. Some preferred materials of construction as well as ranges for various dimensions of the conduits are provided in the aforementioned, co-pending application entitled "Conduits For Use in Placing a Target Vessel in Fluid Communication With a Source of Blood" (Ser. No. 09/393, 131).

Referring now to FIGS. 6 through 17A, one embodiment for manufacturing a conduit according to the invention will be described, the conduit being suitable for use in placing a target vessel of a patient's vascular system in fluid communication with a source of blood. This embodiment uses a molding process to form a conduit having a desired configuration. In particular, the illustrated process can be characterized as an injection molding process in that a moldable material is injected into a mold cavity having a predetermined configuration. It will be appreciated that injection molding (either the same as or varied from that shown in the Figures) is only one possible type of molding procedure that may be used according to this embodiment of the invention.

Figure 6:
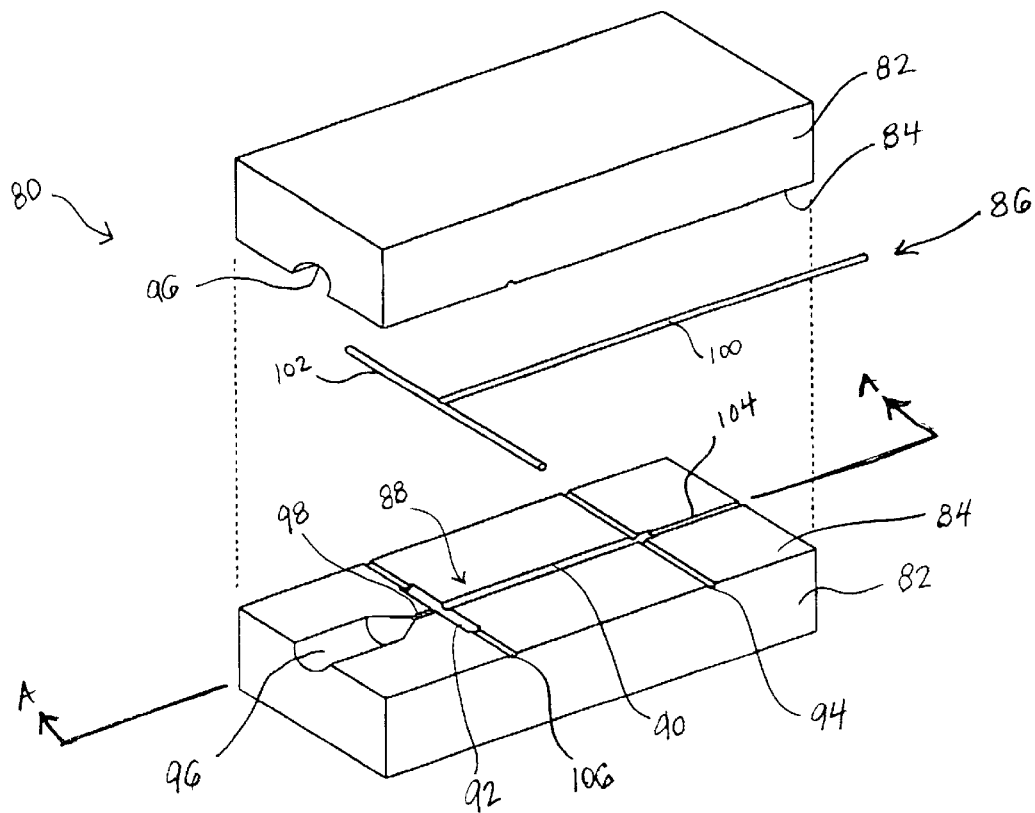
FIG. 6 is an exploded perspective view of a mold and a mandrel for forming a conduit according to one embodiment of the invention, the conduit being sized and configured for use in placing a target vessel of a patient's vascular system in fluid communication with a source of blood.
Figure 6A:
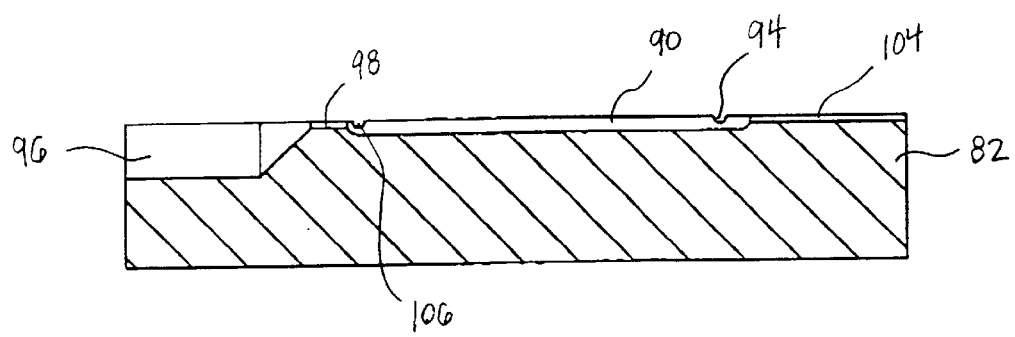
FIG. 6A is a longitudinal sectional view taken along line A—A in FIG. 6.

FIGS. 6 and 6A show a mold 80 including two mold halves 82 which define opposing faces 84 and are adapted to receive a mandrel 86. The mold halves 82 include respective mold cavities 88 which are sized and configured to form a conduit having a predetermined size and shape. In the illustrated embodiment the cavities 88 are mirror images of each other and form a closed cavity when mated. Each cavity 88 includes first and second portions corresponding to first and second portions of the conduit. In particular, the mold cavity 88 of each mold half 82 has a first portion 90 that communicates with and is disposed transverse to a second portion 92, as does the cavity 88 of the other mold half 82 (not shown in the Figures). While the illustrated embodiment includes two mold halves 82, it will be recognized that the mold may comprise a different number of components.

The first and second portions 90, 92 of each mold cavity 88 are preferably provided with one or more channels 94 to vent air and allow excess molding material to flow out of the mold 80. Each mold cavity 88 also has an inlet 96 into which moldable material is injected, the inlet 96 being tapered or necked down at an area 98 communicating with the second portion 92 of the cavity 88. See FIG. 6A. As described below in connection with the Examples, the mold 80 may be formed of any suitable material, for example, a metal such as steel or aluminum, or a nonmetallic material. The mold cavities 88 may be milled or otherwise formed in the mold according to desired specifications.

Figure 7:
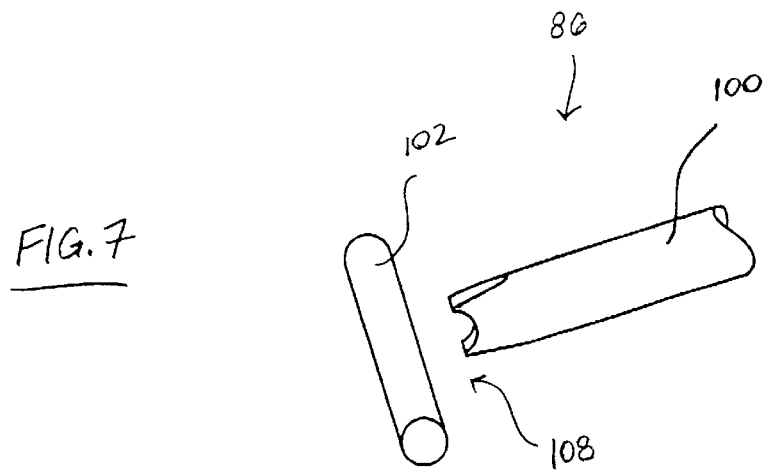
FIG. 7 is an exploded perspective view of a portion of the mandrel shown in FIG. 6.

The mandrel 86 has first and second portions 100, 102 which are received in the first and second portions 90, 92 of each mold cavity 88. More specifically, in addition to the mold cavity 88, each mold half 82 includes a groove 104 for receiving part of the first mandrel portion 100, and a pair of grooves 106 for receiving part of the second mandrel portion 102. The grooves 104, 106 extend from the mold cavity portions 90, 92 and are sized to receive part of the respective mandrel portions 100, 102 in surface-to-surface contact when the mold 80 is assembled. The portions 90, 92, in contrast, are larger than the mandrel portions 100, 102 and grooves 104, 106, as described below regarding FIGS. 15 and 15A–15C. As a result, when the mandrel 86 is placed in the mold 80, an annular space is defined between the mandrel portions 100, 102 and the cavity portions 90, 92 to receive the moldable material. FIG. 7 shows a preferred mandrel configuration wherein the portions 100, 102 are designed to fit snugly together with a minimal profile at their junction 108. The mandrel portions 100, 102 are separated for easy removal from the finished conduit.

Figure 8:
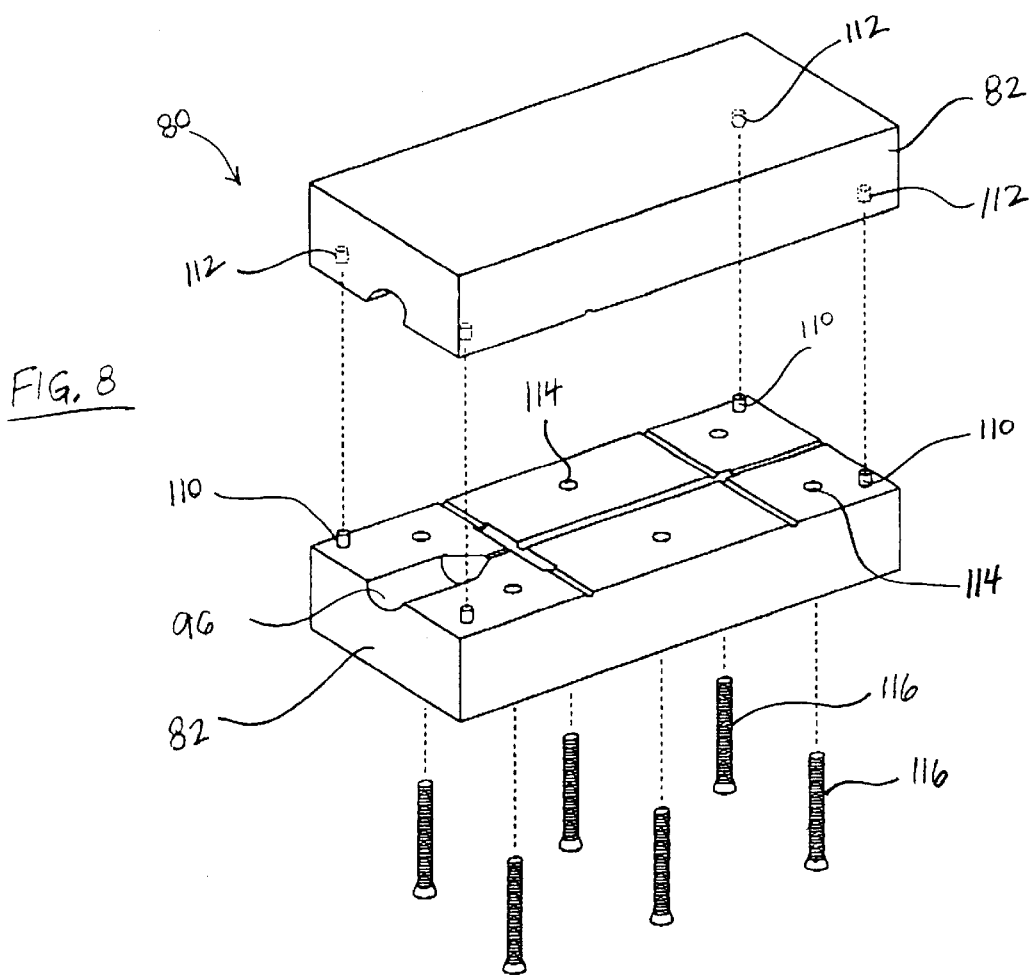
FIG. 8 is an exploded perspective view of the mold shown in FIG. 6, including fasteners for securing the mold portions together.

FIG. 8 shows the mold halves 82 (without the mandrel) along with an exemplary means for aligning and securing the halves together. One mold half 82 is provided with dowel pins 110 which are received in corresponding bores 112 formed in the other mold half. The two mold halves 82 are also provided with mating bores 114 that receive threaded fasteners 116. The fasteners 116 are used to force the mold halves 82 together with their faces 84 tightly sealed to prevent leakage from the mold (beyond that provided by the channels 94). It will be appreciated that alternative or additional means for aligning the mold halves 82 could be used, e.g., a frame that engages the exterior of the mold 80. Similarly, the mold halves 82 may be forced together by alternative or additional means, e.g., a clamp or vise that engages the exterior of the mold 80.

Figure 9:
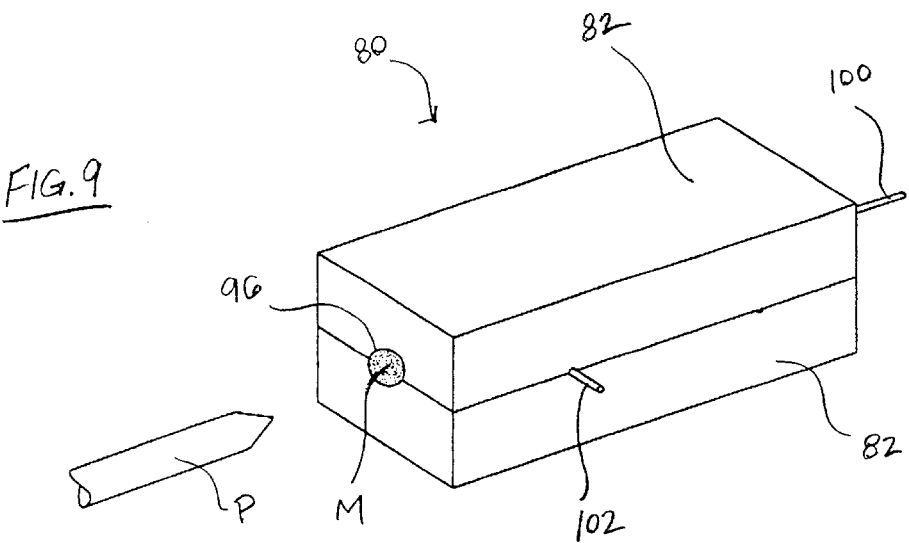
FIG. 9 is a perspective assembled view of the mold showing a moldable material and the mandrel disposed therein.
Figure 10:
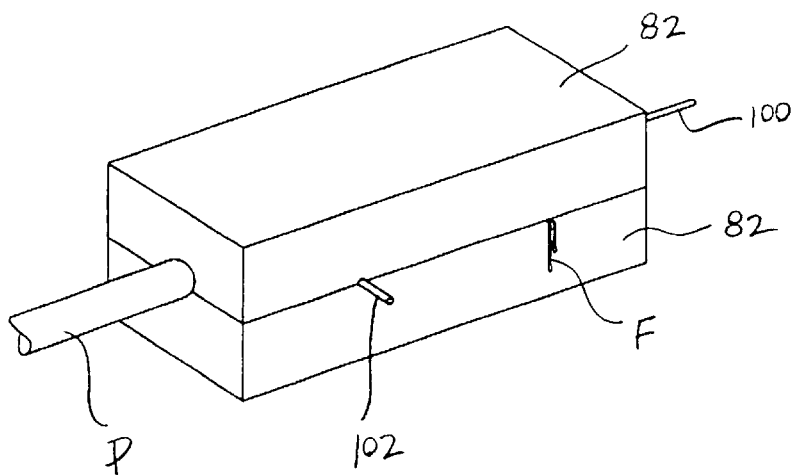
FIG. 10 is a perspective view of the mold illustrated in FIG. 6 showing the moldable material being injected into the mold cavity.

FIG. 9 shows the mold halves 82 and mandrel 86 assembled with the ends of the first and second mandrel portions 100, 102 held in the grooves 104, 106. In the illustrated embodiment the ends of the mandrel portions 100, 102 extend beyond the mold halves 82, but they could instead terminate at or within the mold halves. A release agent is preferably placed on the exterior surface of the mandrel to aid in removing the conduit. A suitable moldable material M is injected into the mold, as can be seen in the inlet 96 in FIG. 9. A plunger P (or other suitable means) is used to inject the material M into the mold to completely fill the cavity 88 around the mandrel 86. FIG. 10 shows the plunger P inserted and a resulting flash F of material M flowing out of the channels 94.

Figure 11:
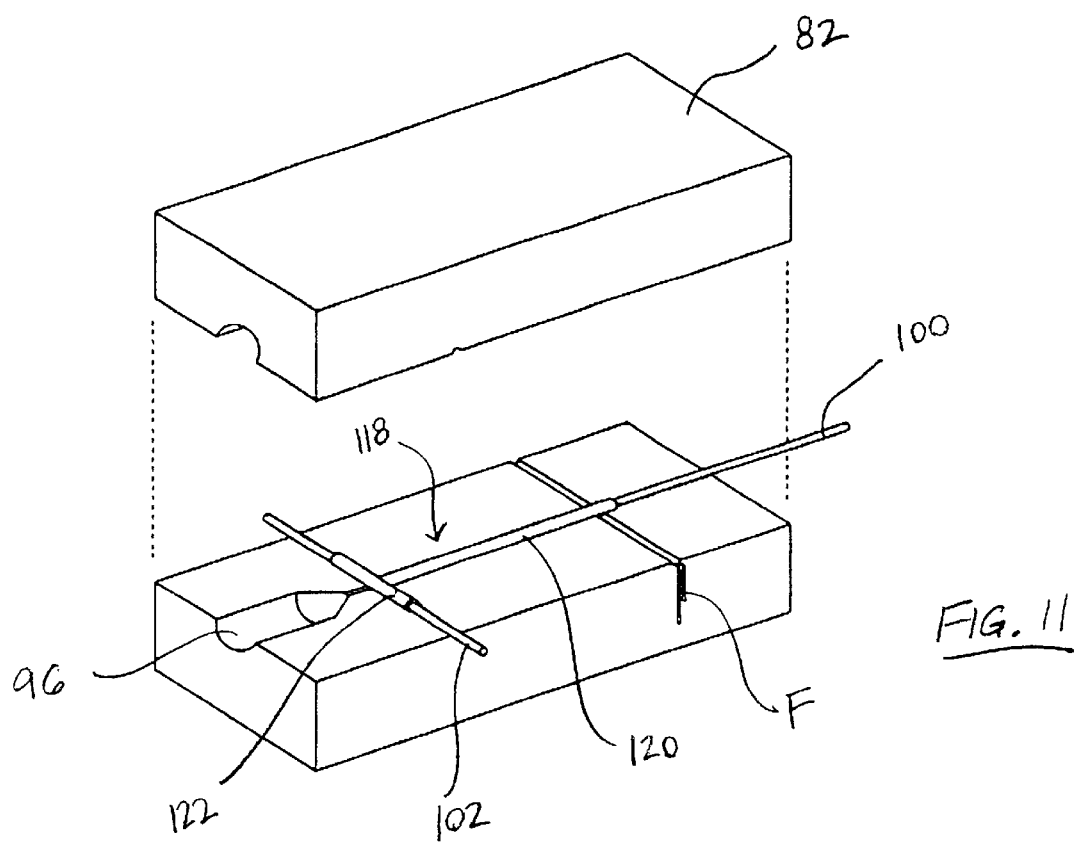
FIG. 11 is a perspective view showing the mold illustrated in FIG. 10 being separated to remove the mandrel.
Figure 12:
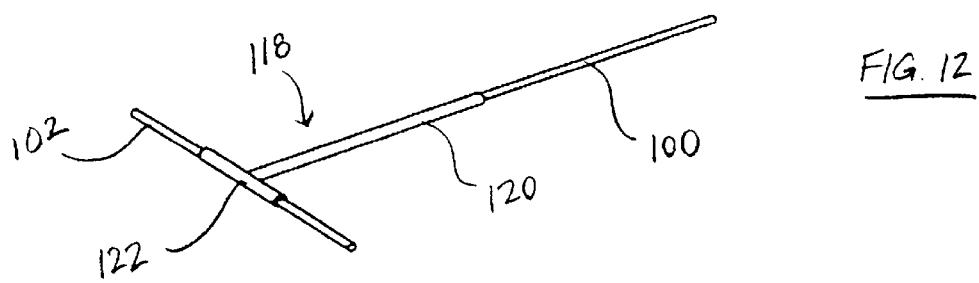
FIG. 12 is a perspective view of the mandrel and the molded preform disposed on the mandrel.

The mold 80 is then subjected to suitable conditions, for example, maintained at a predetermined temperature for a sufficient amount of time, in order to set the material M in the desired configuration. Upon completion of this step, the mold halves 82 are separated, as shown in FIG. 11. The flash F is trimmed and the mandrel 86 is removed from the mold halves 82 along with a molded preform 118 now carried by the mandrel, as shown in FIG. 12. The preform 118 has first and second portions 120, 122, respectively supported by the first and second portions 100, 102 of the mandrel 86. At this point, if desired, the preform 118 may be removed by disassembling the mandrel 86 and subjected to final processing to form a conduit, for example, removing any excess material M, applying any desired coating(s), such as anti-thrombogenic or antibacterial materials, and packaging and sterilizing, such as by placing the device in a Tyvek® pouch that is sterilized by ethylene oxide or gamma radiation. The finished conduit is sterile and ready to be used as a blood delivery device during a cardiovascular procedure.

Figure 13:
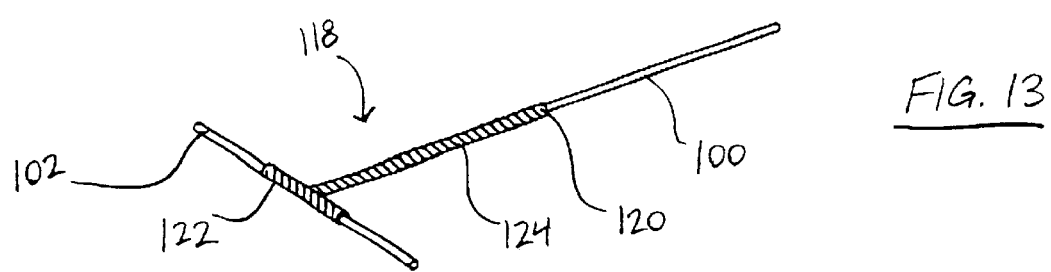
FIG. 13 is a perspective view of the mandrel and molded preform illustrated in FIG. 12 after a reinforcing component has been placed on the preform.

According to a preferred embodiment of the invention, though, the preform 118, prior to final processing, is provided with a reinforcing component to add a desired amount of rigidity to prevent or reduce the likelihood of the conduit collapsing or kinking during use. FIG. 13 shows one possible reinforcing component 124 which is in the form of a wire coil wrapped around all (or alternatively a part of) the preform 118. The wire may be secured to the preform 118 by adhesive or other means in order to remain in place during further processing of the conduit. It will be understood that a component other than wire may be used to reinforce the conduit, for example, as discussed above with respect to the embodiments of FIGS. 1 and 2.

Figure 14:
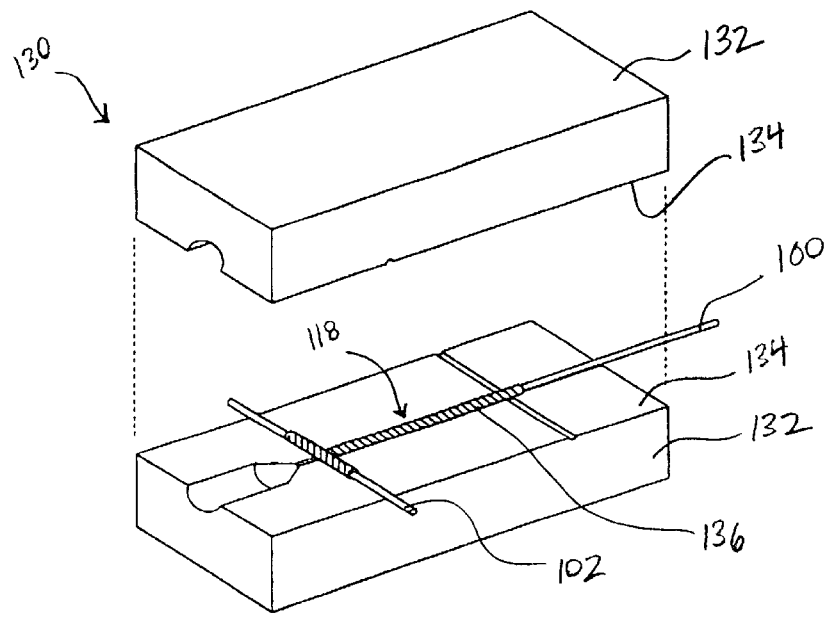
FIG. 14 is an exploded perspective view of another mold constructed according to the invention the mold being sized and configured to receive the mandrel and preform illustrated in FIG. 13.

FIG. 14 shows another mold 130 having a construction essentially the same as the mold 80. The mold 130 has mold halves 132 with mating surfaces 134 and mold cavities 136. The mold cavities 136 are larger than the mold cavities 88 (of the mold 80) in order to accommodate the preform 118 and the reinforcing component 124, both of which are now carried by the mandrel 86, while still providing an annular space around the reinforcing component into which the material M can flow. The mold halves 132 have grooves 138 (not visible in FIG. 14) corresponding to the grooves 104 of mold 80 for receiving the portions 100, 102 of the mandrel.

Figure 15:
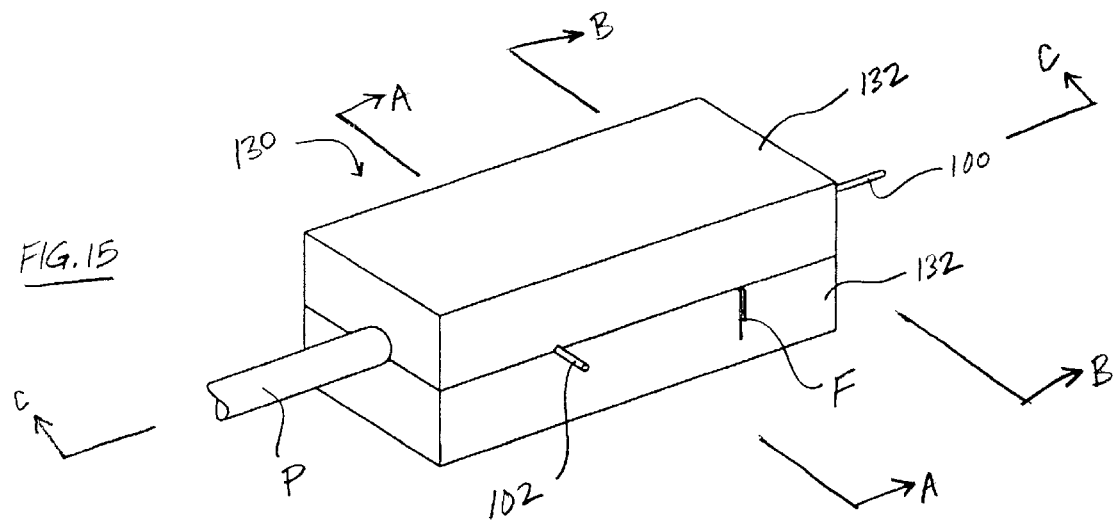
FIG. 15 is a perspective view showing moldable material being injected into the mold illustrated in FIG. 14 to form the preform into a conduit.
Figure 15A:
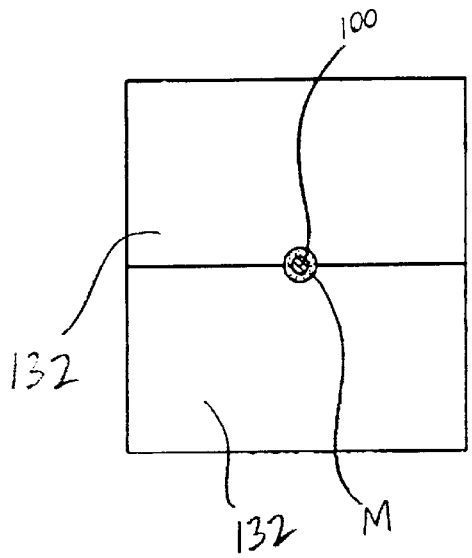
FIGS. 15A and 15B are transverse sectional views taken, respectively, along lines A—A and B—B in FIG. 15.
Figure 15B:
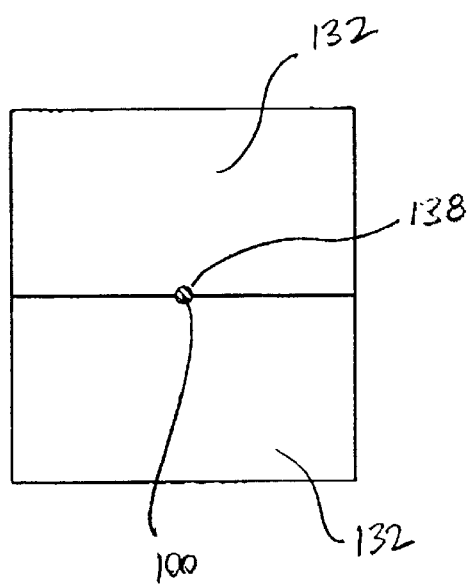
Figure 15C:
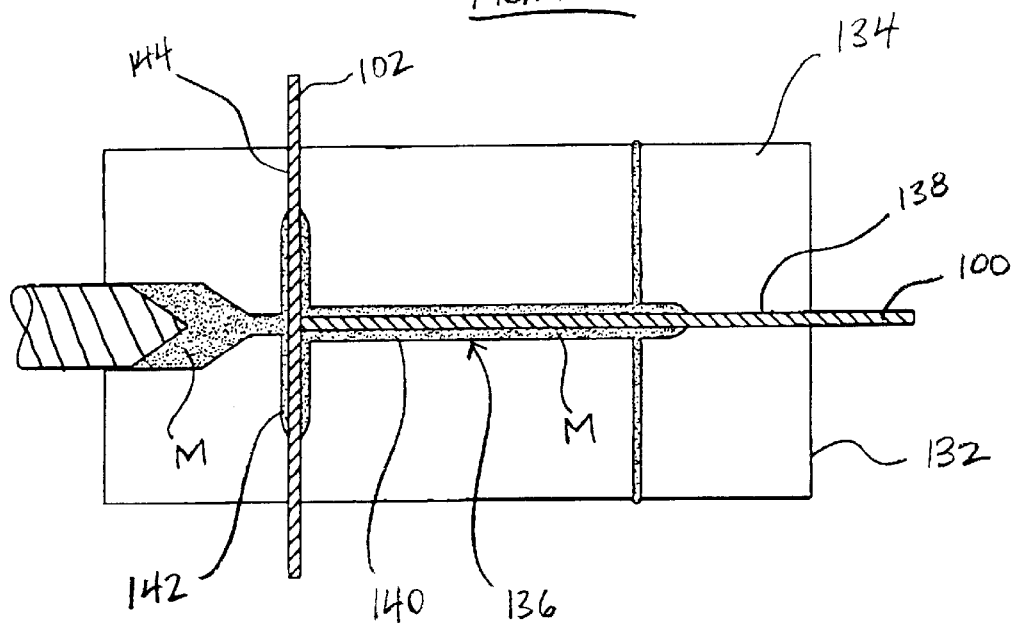
FIG. 15C is a longitudinal sectional view taken along line C—C in FIG. 15.

FIG. 15 shows the mold halves 132 assembled with the mandrel 86 and the reinforced preform 118 disposed therein. The plunger P is shown injecting the material M into the mold 130 with material flash F flowing out of the mold. FIG. 15A is a sectional view through the mold 130 showing moldable material M filling the annular space between the mandrel portion 100 and a first cavity portion 140. FIG. 15B is a sectional view through the mold 130 showing part of the first mandrel portion 100 in surface-to-surface contact with the groove 138. FIG. 15C is a sectional view through the mold showing the groove 138 holding part of the first mandrel portion 100, the groove 144 holding part of the second mandrel portion 102, and the first and second cavity portions 140, 142 filled with material M.

Figure 16:
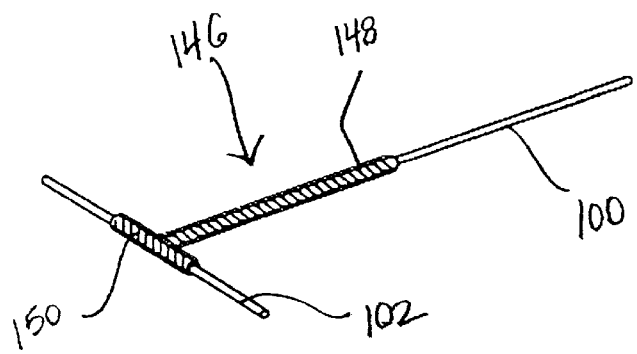
FIG. 16 is a perspective view of the mandrel and conduit after they have been removed from the mold shown in FIG. 15.

The material M is injected and flows around the preform 118 and the reinforcing component 124 (omitted from FIG. 15A for clarity) to fill the mold cavity 136. The mold 130 is then subjected to suitable conditions to set the material M, as explained above with respect to the steps illustrated in FIGS. 11–12. Next, as shown in FIG. 16, the reinforced conduit 146 and the mandrel 86 are removed from the mold 130. As seen from FIG. 15, the second mold cavity portion 142 may have tapered ends so that the second conduit portion 150 has tapered or beveled ends (as does the second portion 14 of the conduit 10 shown in FIG. 1).

Figure 17:
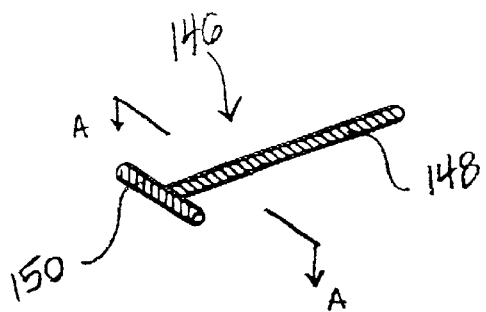
FIG. 17 is a perspective view of the conduit after it has been removed from the mandrel shown in FIG. 16.

Referring to FIG. 16, the mandrel portions 100, 102 are then separated and removed from the conduit 146. As shown in FIG. 17, the conduit 146 includes first and second conduit portions 148, 150 that essentially correspond to the conduit portions 12, 14 of the embodiment shown in FIG. 1. The construction of the illustrated conduit 146 can be seen in FIG. 17A and includes the preform 118, the reinforcing component 124, and a layer 152 of material M (applied in FIG. 15). Also shown is a layer 154 of adhesive, for example, silicone, which is preferably, though not necessarily, applied to the preform 118 to retain the reinforcing component 124 in position, as explained above.

Turning now to FIGS. 18–26, another embodiment for manufacturing a conduit suitable for use in placing a target vessel in fluid communication with a source of blood will be described. This embodiment forms the conduit from one or more pieces of biocompatible material suitable for use in blood contacting applications. The illustrated embodiment forms a conduit from two pieces of material; it will, however, be appreciated that the conduit may comprise fewer or more material pieces. Additionally, it should be appreciated that the specific means by which the material pieces are joined in the illustrated embodiment is exemplary and the invention encompasses alternative means as will be recognized by persons skilled in the art.

Figure 18:
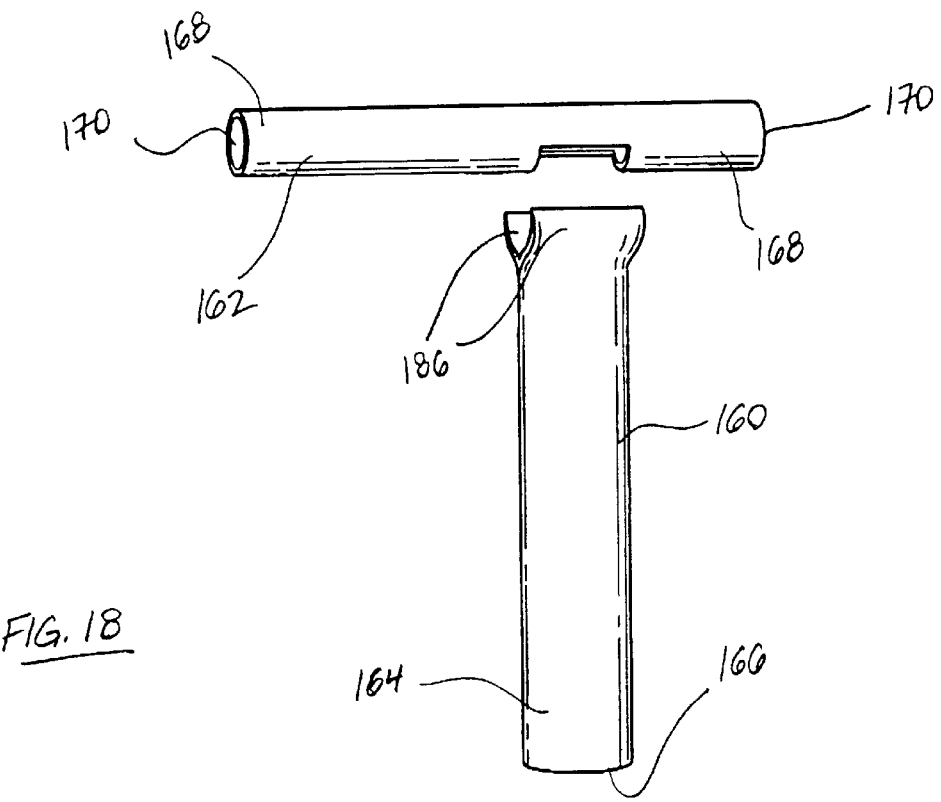
FIG. 18 is an exploded perspective view of components for forming a conduit according to another embodiment of the invention, the components being formed into a desired configuration.
Figure 19:
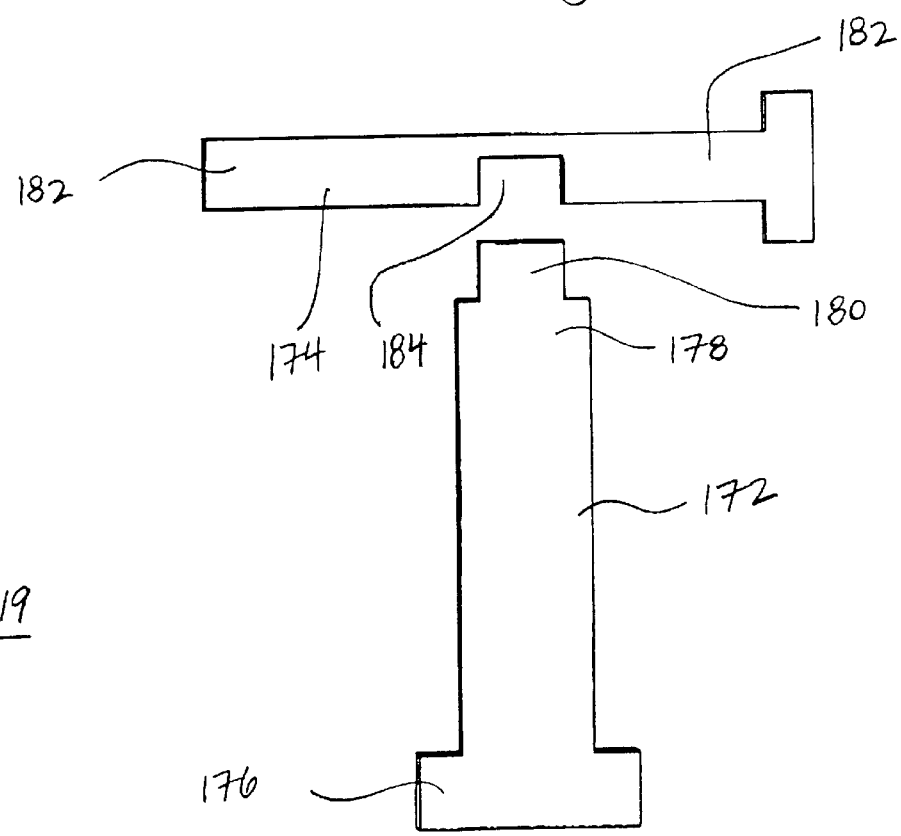
FIG. 19 is an exploded perspective view of a mandrel assembly including two mandrels for use in forming the conduit.

FIG. 18 shows first and second hollow members 160, 162 which are sized and configured for use in placing a coronary blood vessel in fluid communication with a heart chamber containing blood. The first member 160 has an end 164 defining an inlet 166 and the second member 162 has two ends 168 defining outlets 170. The other ends of the members 160, 162 are attached during formation and result in the conduit construction shown in FIG. 2. FIG. 19 shows two mandrels 172, 174 suitable for use in supporting the members 160, 162 during processing. The mandrel 172 has a free end 176 and another end 178 with a tongue 180. The mandrel 174 has two free ends 182 and a notch 184 configured to receive the tongue 180. The mandrel 172 is adapted to be placed in the first hollow member 160 and the mandrel 174 is adapted to be placed in the second hollow member 162, preferably via a tight sliding fit.

Figure 20:
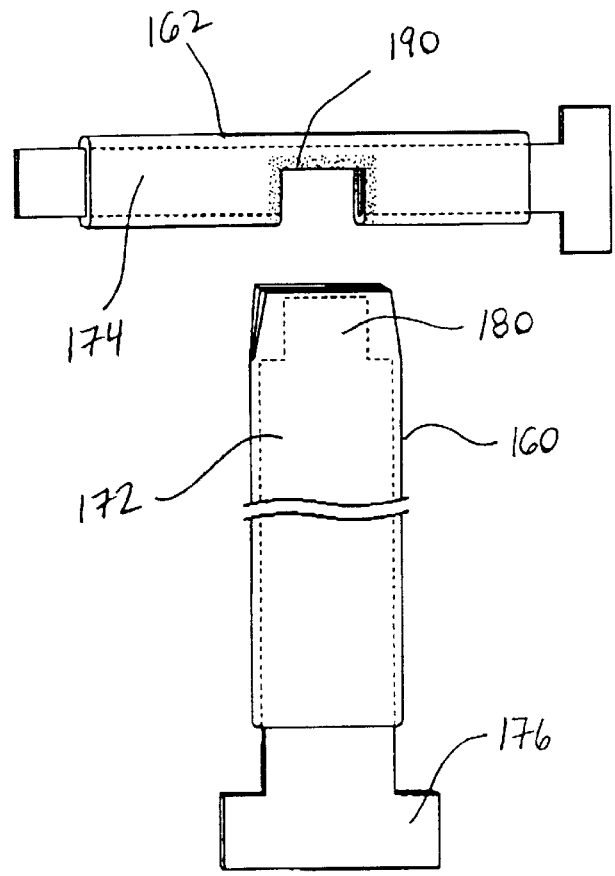
FIG. 20 is an exploded perspective view illustrating the components shown in FIG. 18 mounted on the mandrels shown in FIG. 19.
Figure 21:
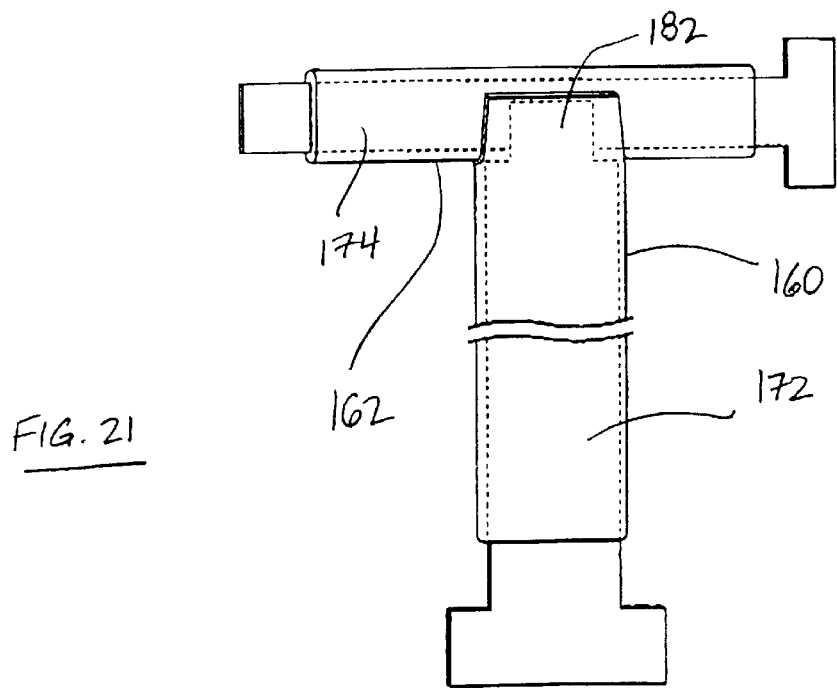
FIG. 21 is a perspective view of the mandrels and components shown in FIG. 20 placed together.

FIG. 20 shows the mandrels 172, 174 inserted into the first and second hollow members 160, 162. The tongue 180 of the mandrel 172 extends to the end of the hollow member 160 between bifurcated flaps 186, while the notch 184 of the mandrel 174 is aligned with a window 188 formed in the second hollow member 162. FIG. 21 shows the mandrels 172, 174 assembled with the first and second hollow members 160, 162 engaged adjacent the tongue 180 and the notch 184 of the mandrels. The flaps 186 extend partially around the exterior of the second hollow member 162; they could alternatively extend fully around the member 162.

Figure 22:
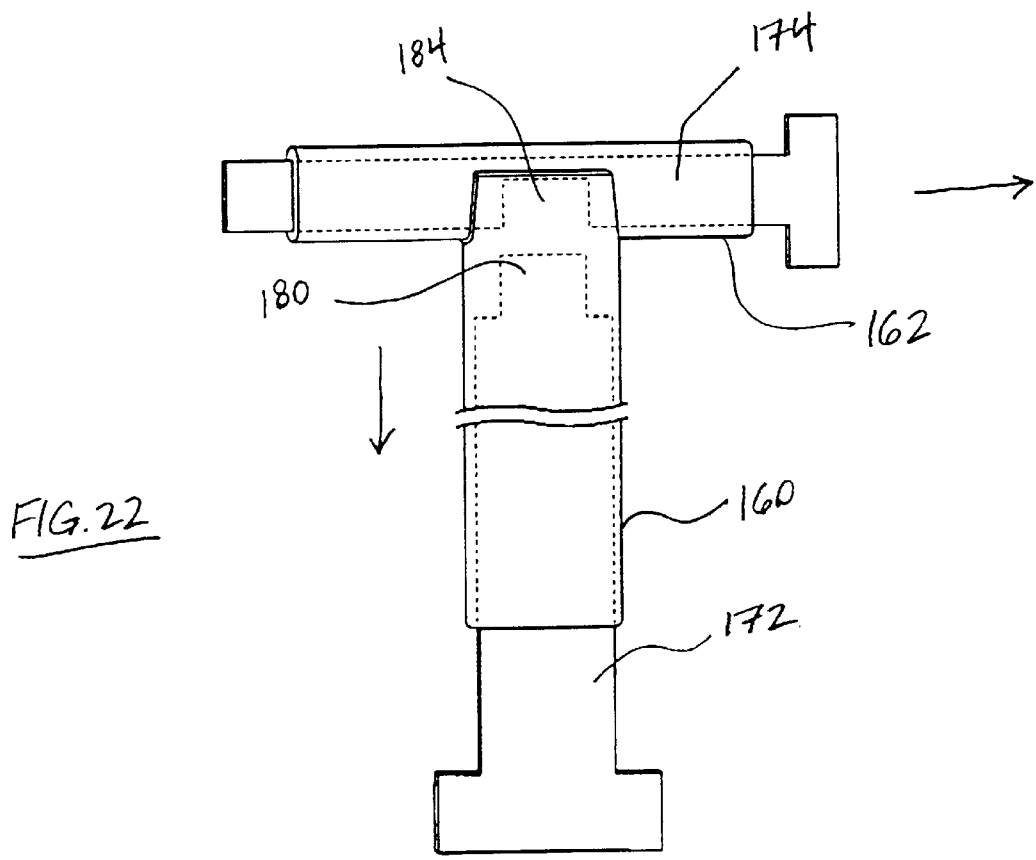
FIG. 22 is a perspective view showing the mandrels illustrated in FIG. 21 being separated.
Figure 23:
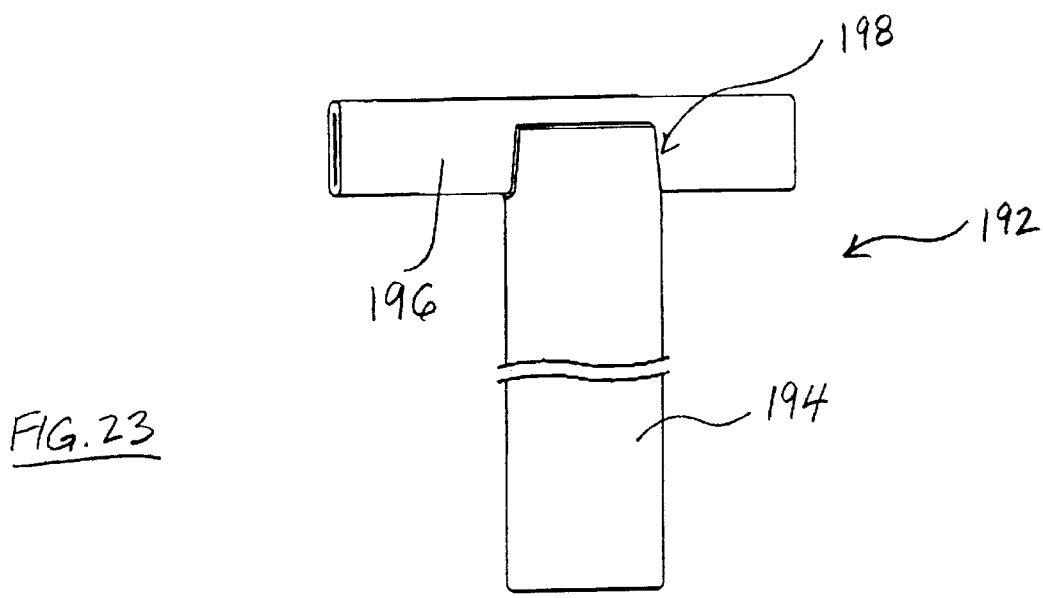
FIG. 23 is an exploded assembled view of the formed conduit after bonding the conduit components and removing the mandrels.

In the illustrated embodiment, prior to placing the flaps 186 of the hollow member 160 against the member 162, a suitable adhesive (indicated schematically at 190 in FIG. 20) is applied to one or both of the hollow members. The mandrels 172, 174 are then moved to the position shown in FIG. 21. The adhesive (or alternative securing means) is subjected to conditions that allow it to bond the first and second hollow members. Next, the mandrels 172, 174 are disassembled, as illustrated in FIG. 22. This results in the conduit 192 shown in FIG. 23, which includes first and second conduit portions 194, 196 (defined by the hollow members 160, 162) secured at a junction 198.

The conduit 192 is ready to be subjected to final processing, for example, trimming or removing any excess material from the conduit and applying any desired coating (s) to the conduit portions, such as anti-thrombogenic or anti-bacterial coatings. The conduit is then ready for packaging and sterilization, for instance, by placing the conduit in a Tyvek pouch the is subjected to ethylene oxide or gamma radiation sterilization. The finished conduit is sterile and ready to be used as a blood delivery device during a cardiovascular procedure.

Figure 24:
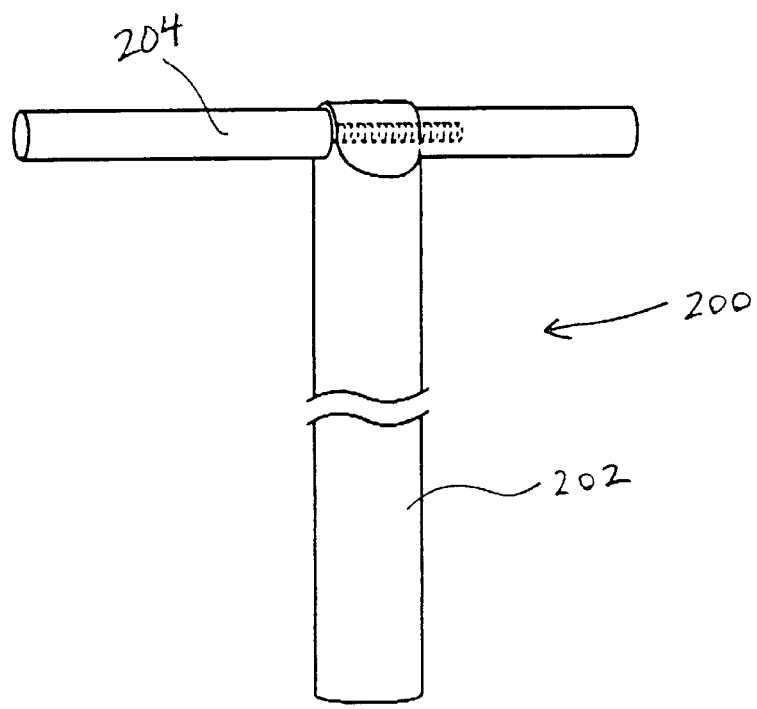
FIG. 24 is an exploded assembled view of an alternative mandrel assembly for use in forming a conduit according to the invention.
Figure 25:
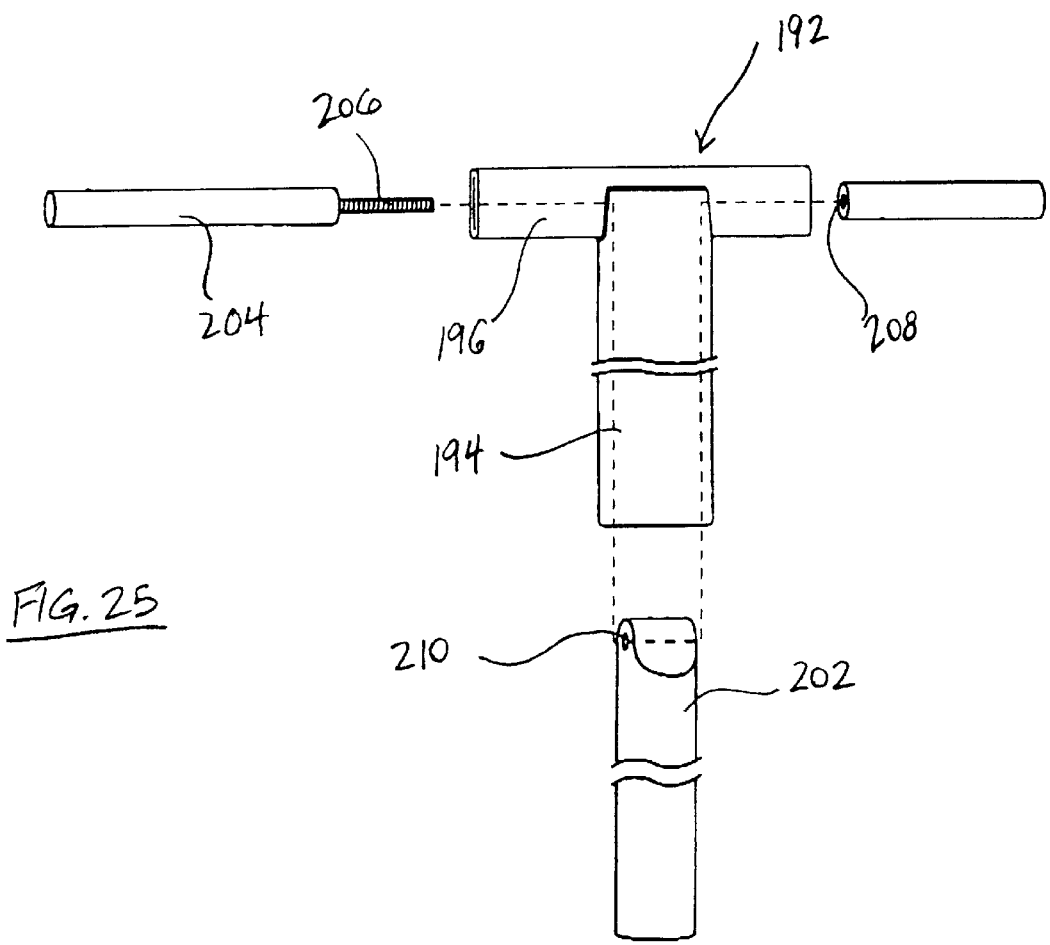
FIG. 25 is an exploded perspective view showing the mandrels of FIG. 24 being placed in the conduit of FIG. 23.
Figure 26:
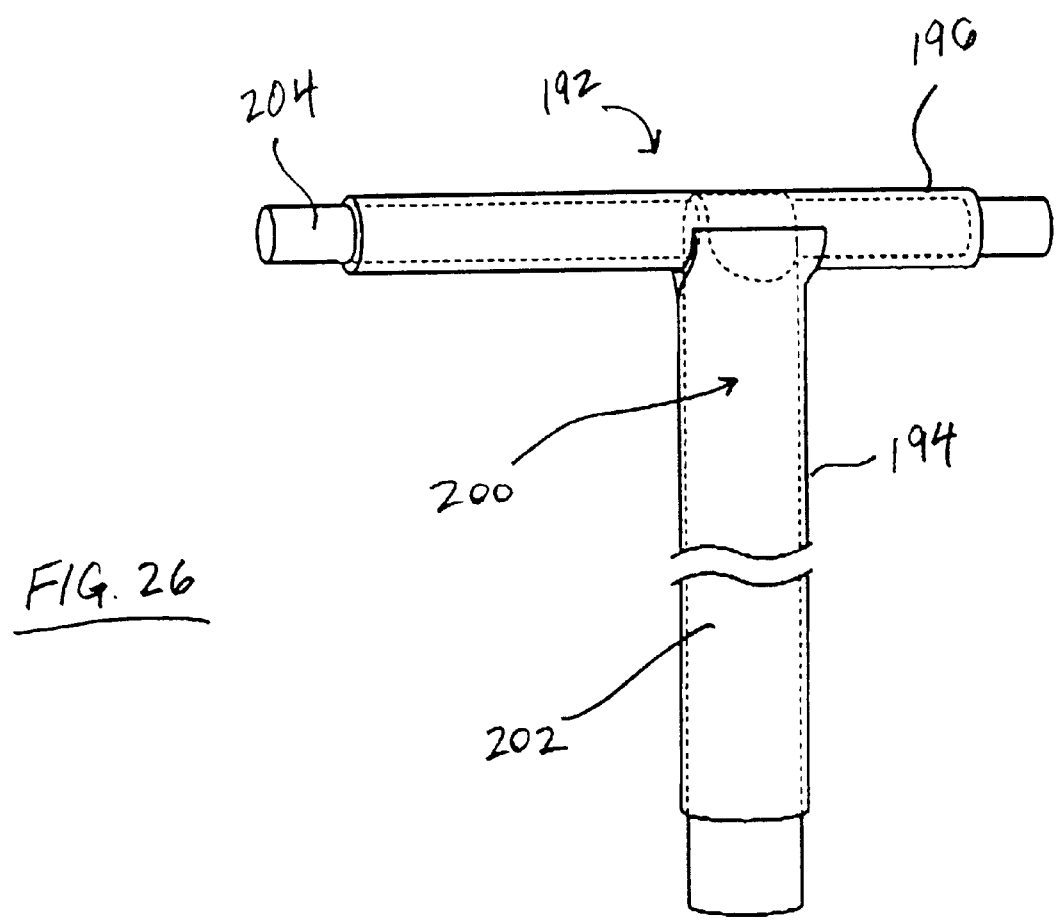
FIG. 26 is a perspective view of the mandrels fully positioned in the conduit shown in FIG. 25.

FIG. 24 shows a mandrel assembly 200 including first and second portions 202, 204 having a desired size and shape for supporting and imparting a particular configuration to the conduit. The mandrel assembly 200 is shown in FIG. 25 along with the conduit 192. The mandrel portion 204 comprises two elements removably secured to each other by a threaded post 206 and bore 208, the post passing through a bore 210 in the mandrel portion 202 to secure the assembly 200. FIG. 26 shows the mandrel assembly 200 supporting the conduit 192. The illustrated mandrel assembly 200 has a round exterior, although other shapes could of course be used, to support similarly or differently configured conduits.

Figure 27:
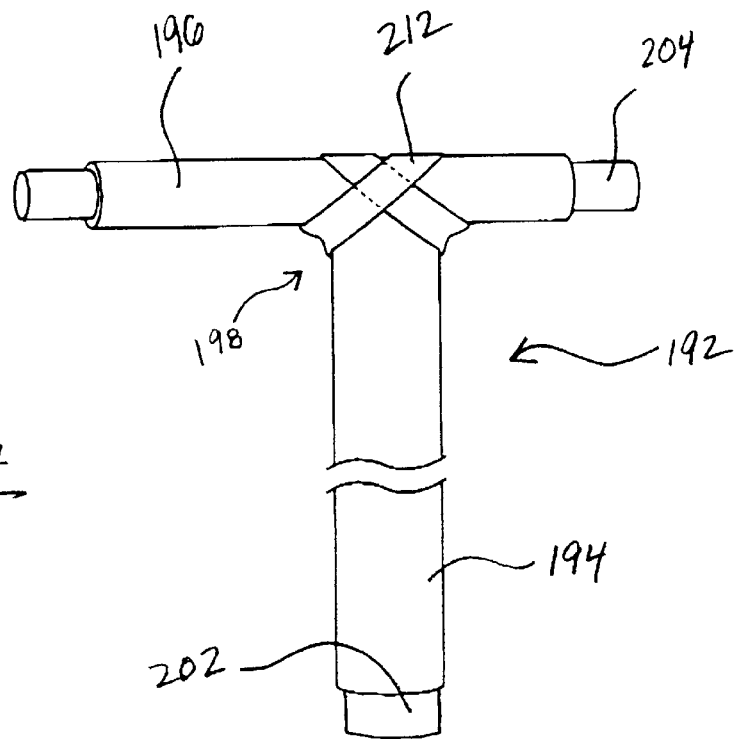
FIGS. 27 and 28 are perspective views of conduits constructed according to alternative embodiments of the invention.
Figure 28:
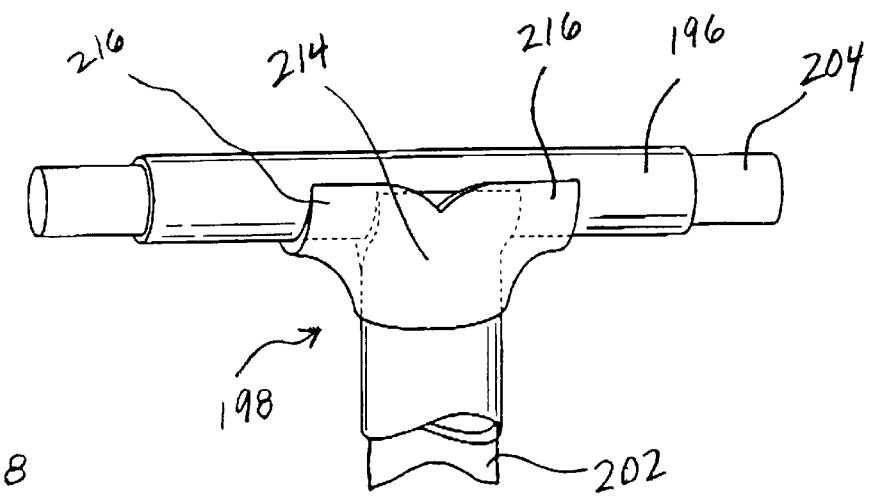

FIGS. 27 shows a further optional step in manufacturing the conduit 192, which is shown supported by the mandrel portions 202, 204. The junction 198 between the first and second conduit portions 194, 196 is provided with a reinforcing component 212. The component 212 is a reinforcing strap wrapped partially or completely around the conduit junction 198. FIG. 28 shows yet another optional step in which an alternative reinforcing component 214 is used to strengthen the conduit junction 198. The component 214 includes bifurcated flaps 216 sized and configured to closely engage the exterior surface of the conduit junction 198. The flaps 216 preferably extend away from the flaps 186 of the first conduit portion 194. This strengthens the junction 198 and enhances hemostasis in use by sealing against the target vessel wall.

Figure 29:
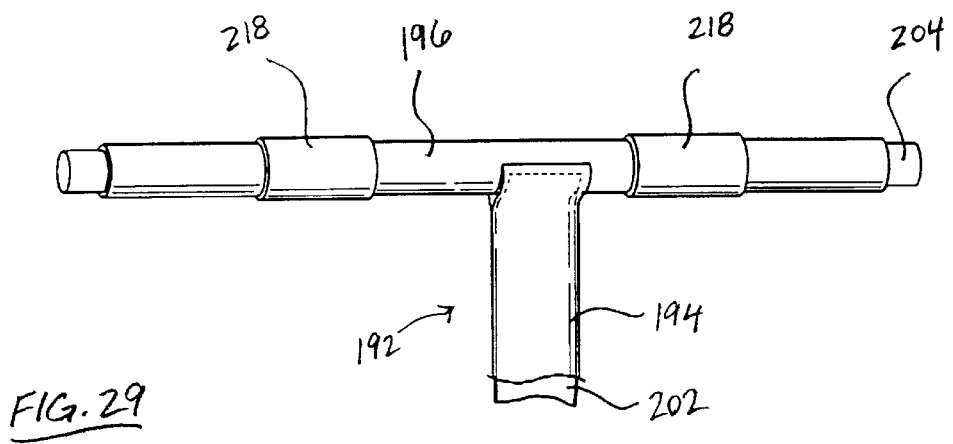
FIGS. 29 and 30 are perspective views showing several conduit manufacturing steps according to another embodiment of the invention.
Figure 30:
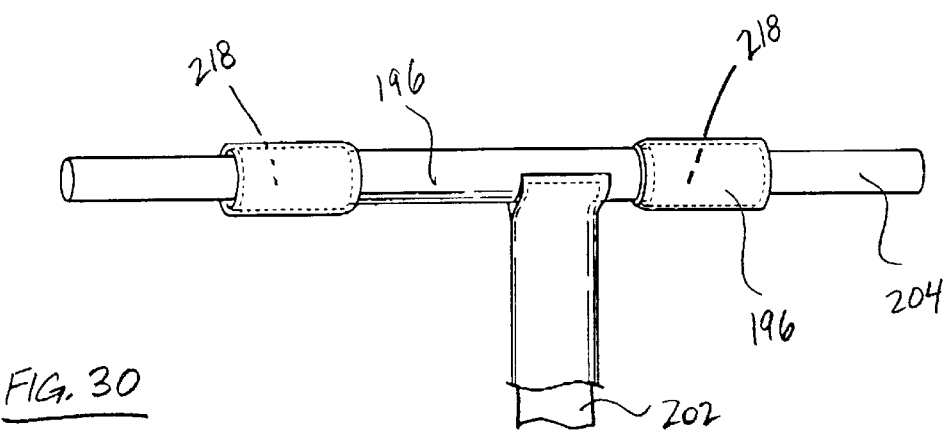
Figure 30A:
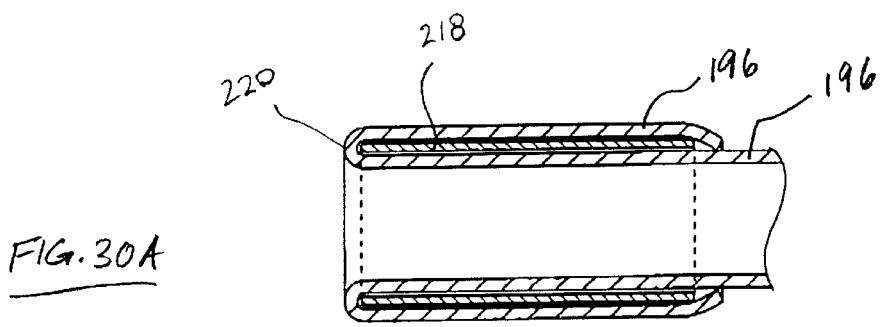
FIG. 30A is a longitudinal sectional view taken through an end of the conduit shown in FIG. 30.

FIGS. 29, 30 and 30A illustrate an alternative method of reinforcing all or a portion of a conduit. The conduit 192 is used again for illustration and is supported by the mandrel assembly 200, as shown in FIG. 29. Reinforcing components 218 in the form of sleeves are slid over the ends of the second conduit portion 196. Adhesive or other means for joining the components may be used. According to the illustrated embodiment, the reinforcing components 114 are arranged so as not to come into direct contact with the luminal surface of the target vessel wall. As shown in FIG. 30, the reinforcing components 218 are disposed on the exterior of the second conduit portion 196, and the ends of the second conduit portion are everted at 220 to capture the reinforcing components 218. This ensures that the material of the second conduit portion (which has beneficial blood interface characteristics) contacts the blood flowing through the target vessel, rather than the reinforcing components 218 (FIG. 30A). It will be understood that while the illustrated reinforcing components are annular and extend around the circumference of the ends of the second conduit portion, they could instead extend around a portion of the ends of the conduit portion.

FIGS. 31 and 32 illustrate an exemplary method of manufacturing a conduit wherein the second portion (received in the target vessel) contacts less than the entire circumferential surface of the vessel wall. The conduit 10 shown in FIG. 1, with first and second conduit portions 12, 14, will be used for sake of example. In the process schematically illustrated in FIG. 31, a conduit is initially formed with a second portion defining a closed (or substantially closed) circumference, and is subjected to a material removal process. This process results in the second conduit portion defining less than a closed circumference, and thus contacting less than the entire luminal surface of the vessel wall when implanted. Further, the preferred conduit design leaves unblocked the posterior portion of the vessel wall and any septal perforators emanating from the section of the vessel being treated.

Avoiding or minimizing contact with the posterior wall is beneficial as it reduces the risk of dislodging stenotic material or otherwise damaging the vessel. However, as shown in FIG. 32, the second conduit portion 14 may nonetheless be provided with a device that engages some of the luminal surface of the vessel wall. For example, the second conduit portion 14 may include the reinforcing component 26 which extends beyond the edges E, as can be seen best from FIG. 31. While the reinforcing component 26 is shown extending 360°, it may extend less than 360°.

The material may be removed by any suitable process, which will depend at least in part on the conduit material. For example, if the conduit, and in particular the second portion of the conduit, is formed of a relatively high durometer material, the process may comprise micro-abrasive media ablation techniques. It will be recognized that the procedure used to remove a desired amount of the material will depend at least in part on the specific material being used.

Figure 33A:
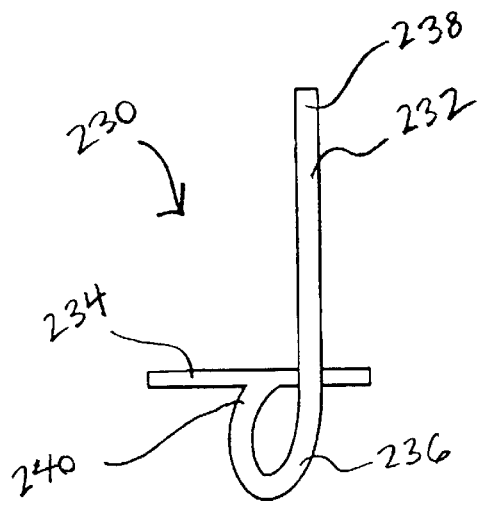
FIGS. 33A–33D are, respectively, front elevation, plan, and side and rear elevation views of a mandrel used to form a conduit according to another embodiment of the invention.
Figure 33B:
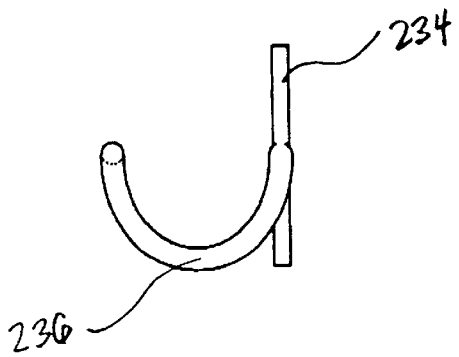
Figure 33C:
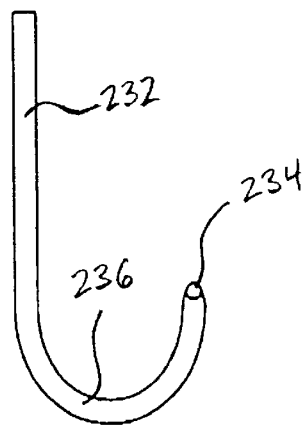
Figure 33D:
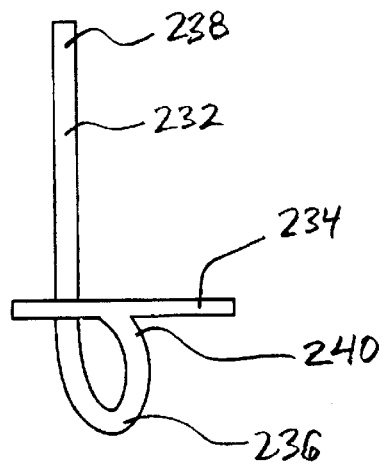

FIGS. 33A–33D and 34A–34E show another embodiment for manufacturing a conduit suitable for use in placing a target vessel in fluid communication with a source of blood will be described. This embodiment forms the conduit by a dip molding process that uses a mandrel having a configuration matching the desired conduit configuration. As shown, a mandrel 230 is formed with first and second portions 232, 234 corresponding, respectively, to the first and second portions of the conduit to be formed. The first mandrel portion is curved as shown in FIG. 33A and includes a bend 236 which directs the remaining portion laterally away from an end 238 of the mandrel portion 232 (the end 238 corresponding to the end of the conduit placed in the heart chamber). The first mandrel portion 232 includes a second bend 240 extending from the first bend 238 to the second mandrel portion 234. The second bend 240 forms a curved transition from the first bend 238 to the second mandrel portion 234 so as to align the portion 234 substantially along the longitudinal axis of the target vessel. The mandrel may be formed of any suitable material, for example, steel.

Figure 34A:
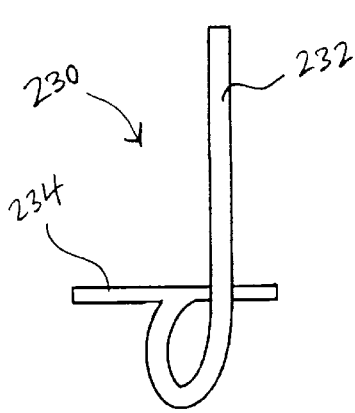
FIGS. 34A–34E are elevation views schematically illustrating the mandrel shown in FIGS. 33A–33D being used to form a conduit.
Figure 34B:
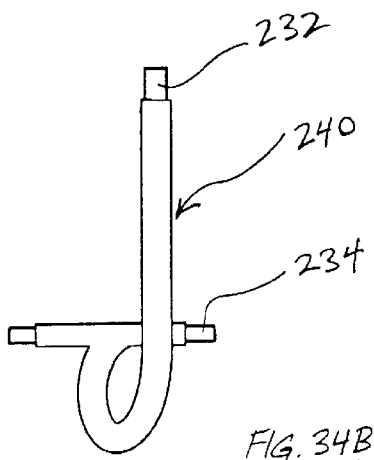
Figure 34C:
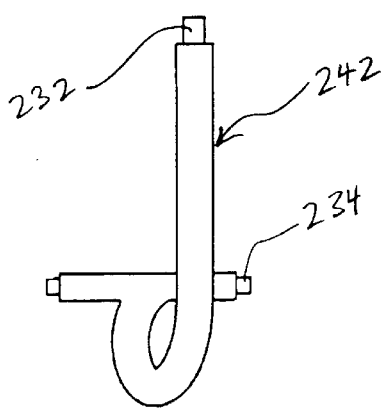
Figure 34D:
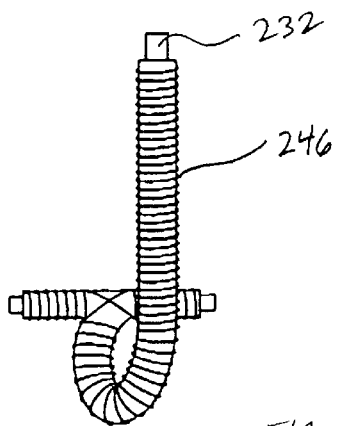
Figure 34E:
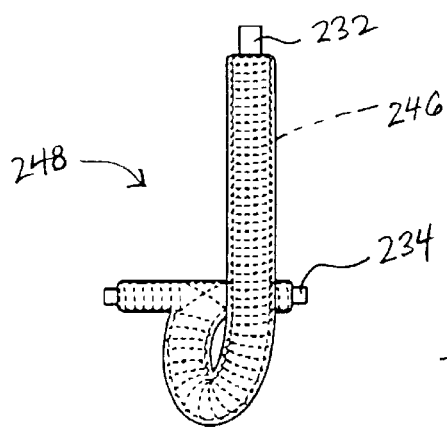

FIGS. 34A–34E schematically illustrate using the mandrel 230 shown in FIGS. 33A–33D in a dip molding process to form a conduit for use in placing a target vessel in communication with a heart chamber containing blood. The mandrel 230 (FIG. 34A) is preferably treated with a mold release and then dipped into a container of moldable material, for example, NuSil MED-6210, commercially available from NuSil Technology of Carpinteria, Calif. The silicone is cured and produces a preform 240 (FIG. 34B). The mandrel is preferably manipulated by being rotated in multiple directions to promote even flow of silicone and avoid bubbles or uneven dispersion on the mandrel. The mandrel and preform 240 are dipped again and the silicone cured to produce a preform 242 (FIG. 34C). A reinforcing component in the form of a coil spring 246 is wrapped on the preform (FIG. 34D). The assembly is dipped again in silicone and then cured to produce a conduit 248 (FIG. 34E).

It will be recognized that the illustrated injection and dip-molding procedures are exemplary only in that other molding procedures may be used to form the conduit. As an example, a suitable rotational molding process may be used to manufacture conduits according to the invention. Other molding processes may of course be used as well.

The methods and devices of the invention have been used to produce various types of conduits that have been implanted in animals and have successfully delivered blood from a source to a target vessel. In the animal studies the source of blood was the left ventricle and the target vessel was a coronary artery. Three examples are presented below.

EXAMPLE 1

A first mold including two mold halves was machined from aluminum and had a configuration substantially the same as that shown in FIG. 6. The mold halves were connected via dowel pins and grooves were milled into the faces of the mold halves. The grooves defined a cavity with first and second portions disposed transverse to each other to form a conduit having the same configuration. The first and second cavity portions were sized to receive a steel mandrel, and the cavities and the mandrel substantially corresponded to those shown in FIG. 6.

A light coating of spray-on mold release was applied to the mandrel, and the mandrel was placed in the mold halves which were then assembled. Silicone was used as the moldable material. Air was removed from the silicone by vacuum and ultrasonic agitation prior to injecting the silicone into the mold cavity. Next, approximately one cc of NuSil Med-4950 silicone was poured into the inlet of the mold to form the conduit preform (as this conduit included a reinforcing component), and a plunger was used to force the material further into the mold inlet. Air was removed from the mold by applying a vacuum, and then the plunger was used to further force the silicone into the mold cavity.

The silicone was cured by heating the mold to 15° C. for 1 hour. The mold cooled and the halves separated after trimming the excess material from the gates. The mandrel and molded conduit were removed and washed with water and alcohol and then allowed to dry. Next, a reinforcing component was added. Nitinol coils were prepared with both left and right-hand pitch directions for the different conduit portions from a length of nitinol wire. A first right-hand coil was wrapped around the first conduit portion and a second right-hand coil was wrapped around one leg of the second conduit portion, at the same pitch. A similarly sized left-hand coil was wrapped around the other leg of the second conduit portion at the same pitch (with the outermost ends of the coils boxed with a smaller pitch). The two coils were wrapped around the second conduit portion with one turn extending across the junction.

Figure 17A:
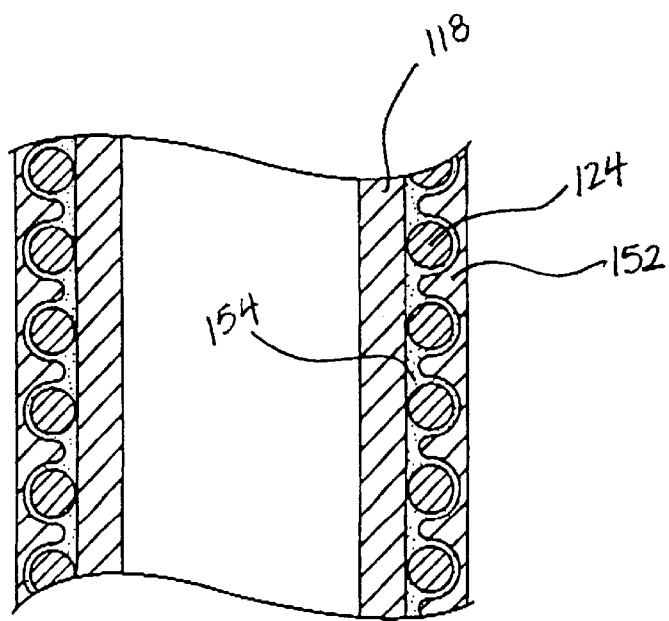
FIG. 17A is a longitudinal sectional view taken along line A—A in FIG. 17.

Before wrapping the coils, NuSil Med-6210 silicone was applied to the preform to help secure the coils to the conduit, as shown by the embodiment of FIG. 17A. The coils were then wrapped and the mandrel placed in a second mold configured the same as the first mold but larger to accommodate the conduit preform and reinforcing component now carried by the mandrel. NuSil Med-4950 silicone was injected into the second mold and the mold was heated to set the silicone and bond the respective components, in accordance with the steps already used to produce the conduit preform. The mandrel was then removed and disassembled to allow the conduit and mandrel to be separated.

A device for establishing flow communication with a heart chamber, such as the device 66 described above with respect to FIGS. 4A–4C, was secured to the distal end portion of the first portion of the conduit. The conduit was sterilized and ready for use by being implanted in an animal heart to deliver blood from a heart chamber, such as the left ventricle, to a target vessel, such as the left anterior descending coronary artery.

EXAMPLE 2

Two tubular lengths of expanded PTFE (ePTFE) having a wall thickness of 0.008 inch and an internodal distance of 30 microns were formed substantially as the two conduit portions shown in FIG. 18. Mandrels were coated with a release agent and were used to support the two pieces of ePTFE while they were joined. Silicone was placed between the two portions at the junction and the silicone was cured in an oven at 150° for 2 hours to bond the two portions; the silicone, NuSil Med-6640 wicked between the nodes of the ePTFE and when cured bonded the pieces together to produce a conduit preform having two portions with lumens in fluid communication.

A reinforcing component was applied by wrapping a nitinol wire around the first and second conduit portions. The exterior surface of the conduit preform was coated with NuSil Med-4850 (LSR) silicone and the reinforcing wire was wrapped around the preform, embedding itself in the silicone. The silicone was then cured again in an oven at 150° for 1 hour. The resulting conduit included a layer of silicone over the coils of the reinforcing component to prevent their direct contact with animal tissue. The mandrels were disassembled and a device for communicating with a heart chamber was coupled to the first conduit portion. The device was then ready to be sterilized and placed in a target vessel of an animal heart.

It should be understood that reinforcing components, layers, etc., are preferred but not necessary, such components preferably taking the form of those disclosed in the aforementioned co-pending application (Ser. No. 09/393,131). Also, if intended for use in an application with a heart chamber as the blood source, the conduit may be provided with a device for facilitating communication with the heart chamber, and preferably preventing or minimizing blockage of the conduit. Suitable devices are disclosed in co-pending, commonly owned application Ser. No. 09/304,140, filed on May 3, 1999 and entitled "Methods and Devices for Placing a Conduit in Fluid Communication With a Target Vessel," the entire subject matter of which is incorporated herein by reference.

The conduits manufactured according to the invention may include a valve or other means for controlling or regulating blood flow. Suitable valves, as well as means for measuring myocardial thickness or verifying entry into the heart chamber, are disclosed in application Ser. No. 09/023,492, filed on Feb. 13, 1998, and entitled "Methods and Devices Providing Transmyocardial Blood Flow to the Arterial Vascular System of the Heart," the entire subject matter of which has been incorporated herein by reference. Likewise, the conduits may be provided with a reservoir for retaining and discharging blood in a desired manner.

The conduits of the invention may be manufactured as part of, or for coupling to, a conduit delivery device, such as that disclosed herein. The conduits and delivery devices manufactured according to the invention may be sized and configured differently from that specifically illustrated in the Figures. For instance, the cross-section of one or more portions of the conduit may be noncircular, e.g., elliptical, to better match the profile of the target vessel. As a further example, the delivery device may be relatively short with the shaft assembly substantially rigid for use in an open-chest procedure. Alternatively, the delivery device may be configured for use in either a minimally invasive or endovascular procedure, wherein the actuators for controlling the device components are located adjacent the proximal end of the device to allow remote deployment of the conduit, for example, as disclosed in the aforementioned, co-pending, commonly-owned application Ser. No. 09/304,140.

It will be appreciated that the features of the various embodiments of the invention may be used together or separately, while the manufacturing methods and devices disclosed herein may be modified or combined in whole or in part. As an example, more than one conduit may be formed as part of (or coupled to) a manifold that is placed in communication with one source of blood so as to deliver blood to multiple target vessels. The conduits and devices of the invention may include removable or detachable components, could be formed as disposable instruments, reusable instruments capable of being sterilized, or comprise a combination of disposable and reusable components.

Further, it will be understood that the invention may be used to manufacture conduits for use in specific types of medical procedures, for example, an open surgical procedure including a median sternotomy, a minimally invasive procedure utilizing one or more relatively small access openings or ports, or an endovascular procedure using peripheral access sites. Similarly, the conduits may be designed for use in beating heart procedures, stopped-heart procedures utilizing cardiopulmonary bypass (CPB), or procedures during which the heart is intermittently stopped and started.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for manufacturing a conduit for use in placing a target vessel of a patient's vascular system in communication with a heart chamber containing blood, the method comprising:
   a. providing a biocompatible material suitable for use in delivering blood from one location to another location;
   b. molding the biocompatible material into a conduit comprising first and second portions that are disposed transverse to each other and have respective lumens in communication;
   c. wherein the molding step is performed so that the first conduit portion is configured to be placed in communication with the heart chamber containing blood and is substantially rigid to prevent the first portion collapsing during contraction of myocardial tissue; and
   d. wherein the molding step is performed so that the second conduit portion is configured to be placed in communication with the target vessel and is substantially resilient to allow the second conduit portion to be disposed within the target vessel lumen and substantially conform to the contour of the target vessel.

2. The method of claim 1, wherein the biocompatible material is molded into a conduit configuration including first and second portions disposed transverse to each other to form an acute angle.

3. The method of claim 2, wherein the moldable material comprises a silicone polymer.

4. The method of claim 2, wherein steps (b), (c) and (d) are performed to mold the material into a conduit including first and second portions that are substantially perpendicular.

5. The method of claim 2, wherein steps (b), (c) and (d) comprise an injection molding procedure.

6. The method of claim 1, wherein the biocompatible material is non-moldable material and step (b) is performed by fabricating the material into a conduit configuration.

7. The method of claim 1, further comprising providing the first conduit portion with a device configured to be positioned at least partially in tissue that is disposed adjacent a heart chamber containing blood.

8. The method of claim 1, further comprising providing at least one of the first and second portions of the conduit with a reinforcing component.

9. The method of claim 1, wherein step (b) comprises forming the second conduit portion with two outlets facing in different, substantially opposite directions.

10. A method for manufacturing a conduit for use in placing a target vessel of a patient's vascular system in fluid communication with a source of blood, the method comprising steps of:
   a. providing a mold having a cavity configured to form a conduit including first and second portions disposed transverse to each other, wherein a conduit formed corresponding to the cavity is suitable for use in placing a source of blood in fluid communication with the lumen of a target vessel:
   b. placing a biocompatible moldable material in the mold cavity;
   c. subjecting the material to conditions that mold the material into a conduit having said first and second portions; and
   d. separating the mold and the conduit;
   e. wherein the second portion of the conduit is configured to be placed in the lumen of the target vessel and is formed so as to at least partially conform to the target vessel.

11. The method of claim 10, wherein step (b) comprises injecting the biocompatible moldable material into the mold cavity and removing any gas from the material.

12. The method claim 10, wherein the molded conduit is generally T-shaped with the first and second portions of the conduit substantially perpendicular.

13. The method of claim 10, wherein the biocompatible moldable material comprises a silicone polymer.

14. The method of claim 10, wherein the silicone polymer is polydimethylsiloxane.

15. A method for manufacturing a conduit for use in placing a target vessel of a patient's vascular system in fluid communication with a source of blood, the method comprising the steps of:
   a. providing a mold having a cavity including first and second portions disposed transverse to each other;

b. positioning a mandrel in the mold cavity, the mandrel having first and second portions substantially corresponding to the first and second portions of the mold cavity;

c. forcing a moldable material into the mold cavity and around the first and second portions of the mandrel into the first and second portions of the mold cavity;

d. subjecting the material to conditions sufficient to set the material in a desired configuration;

e. removing the mandrel from the mold; and f. separating the mandrel and the material to produce a conduit comprising first and second portions that are disposed transverse to each other and have lumens in fluid communication with each other g. wherein the second portion of the conduit is configured to be placed in the lumen of the target vessel and is formed so as to at least partially conform to the target vessel.

16. The method of claim 15, wherein the moldable material is a silicone polymer, and step (d) comprises heating the material to a temperature sufficient to set the material in a desired configuration.

17. The method of claim 15, further comprising applying a release agent to the mandrel prior to performing step (c).

18. A method for manufacturing a conduit for use in a medical procedure that places a target vessel in fluid communication with a source of blood in a patient's body, the method comprising steps of:

a. providing a mandrel including first and second portions disposed transverse to each other, the first and second portions of the mandrel defining at least one external surface corresponding to an interior surface of a desired conduit configuration;

b. disposing a biocompatible moldable material on the external surface of the mandrel;

c. subjecting the material to conditions that mold the material into a conduit having the desired configuration; and d. separating the conduit from the mandrel;

e. wherein the second portion of the conduit is configured to be placed in the lumen of the target vessel and at least partially conform to the target vessel.

19. The method of claim 18, further comprising placing a release coating on the mandrel, and wherein step (b) is performed by dipping the coated mandrel in the biocompatible moldable material.

20. The method of claim 18, wherein the mandrel is generally T-shaped and the conduit has first and second portions that are substantially perpendicular.

21. The method of claim 18, wherein the mandrel is generally T-shaped with the first and second portions defining a curved path including at least two bends.

22. The method of claim 18, further comprising attaching a reinforcing component to at least a portion of the conduit to prevent collapse or kinking of the conduit.

23. The method of claim 18, further comprising packaging and sterilizing the conduit to provide a sealed, sterile blood delivery device ready to be used in a cardiovascular procedure.

* * * * *